United States Patent [19]

Goodman et al.

[11] Patent Number: 5,945,312
[45] Date of Patent: Aug. 31, 1999

[54] SYNTHESIS OF FLUOROPHORE-LABELED DNA

[75] Inventors: Myron F. Goodman, La Canada, Calif.; Linda J. Reha-Krantz, Edmonton, Canada

[73] Assignees: University of Southern California, Los Angeles, Calif.; University of Alberta, Edmonton, Canada

[21] Appl. No.: 08/966,145

[22] Filed: Nov. 7, 1997

Related U.S. Application Data

[62] Division of application No. 08/632,742, Apr. 15, 1996, abandoned.

[51] Int. Cl.$^6$ ....................................................... C12P 19/34
[52] U.S. Cl. ............................ 435/91.1; 435/6; 435/270; 536/23.1; 536/24.3; 436/94; 436/173
[58] Field of Search ............................... 435/6, 91.1, 220; 436/94, 173; 536/23.1, 24.3

[56] References Cited

U.S. PATENT DOCUMENTS 4,711,955  12/1987  Ward et al. ............................. 536/23.1

OTHER PUBLICATIONS

Delarue et al., "An Attempt to Unify the Structure of Polymerase," *Protein Engineering*, 3(6), 461–467 (1990).

Reha–Krantz et al.(I), "Bacteriophage T4 DNA Polymerase Mutations That Confer Sensitivity to the PP$^i$ Analog Phosphonoacetic Acid," *J. Virology*, 67(1), 60–66 (Jan. 1993).

Reha–Krantz et al.(II), "Genetic and Biochemical Studies of Bacteriophage T4 DNA Polymerase 3'→5'–Exonuclease Activity," *J. Biological Chemistry*, 268(36), 27100–27108 (Dec. 1993).

Stocki et al., "Dynamics of Bacteriophage T4 DNA Polymerase Function: Identification of Amino Acid Residues that Affect Switching Between Polymerase and 3'→5' Exonuclease Activity," *J. Molecular Biology*, 254, 15–28 (1995).

Delarue, M., et al., "An attempt to unify the structure of polymerases", *Protein Engineering*, 3(6)461–467 (1990).

Reha–Krantz, L. J., et al., "Bacteriophage T4 DNA Polymerase Mutations That Confer Sensitivity to the PP$^i$ Analog Phosphonoacetic Acid", *J. Virol.*, 67(1):60–66 (1993) (Jan.).

Reha–Krantz, L. J., et al., "Genetic and Biochemical Studies of Pacteriophage T4 DNA Polymerase 3'→5'–Exonuclease Activity", *J. Biol. Chem.*, 268(36):27100–27108 (1993)(Dec.).

Stocki, S.A., et al., "Dynamics of Bacteriophage T4 DNA Polymerase Function: Identication of Amino Acid Residues that Affect Switching between Polymerase and 3'→5' Exonuclease Activites", *J. Mol. Biol.*, 254:15–28 (1995).

*Primary Examiner*—Marian C. Knode
*Assistant Examiner*—L. Eric Crane
*Attorney, Agent, or Firm*—Fulbright & Jaworski L.L.P.

[57] ABSTRACT

Sequencing methods and methods for synthesizing DNA probes using mutant bacteriophage T4 DNA polymerases which have increased ability to incorporate modified nucleotides for the synthesis of long or short chains of complementary, modified, e.g., fluorophore-labeled DNA. In general, the mutant T4 DNA polymerases retain 3'→5' exonuclease activity; hence, reduction or elimination of 3'→5' exonuclease activity is not a prerequisite for efficient synthesis of a complementary fluorophore-labeled or other modified DNA. In fact, retention of 3'→5' exonuclease activity increases accuracy of DNA replication, because these exonucleases proofread or edit the product of DNA replication.

23 Claims, 13 Drawing Sheets

Formula: $C_{42}H_{45}N_8O_{19}P_3Li_4$

Rh = rhodamine
Rhodamine-12-dUTP

Formula: $C_{42}H_{45}N_8O_{19}P_3Li_4$

FIG. 1E  R = rhodamine
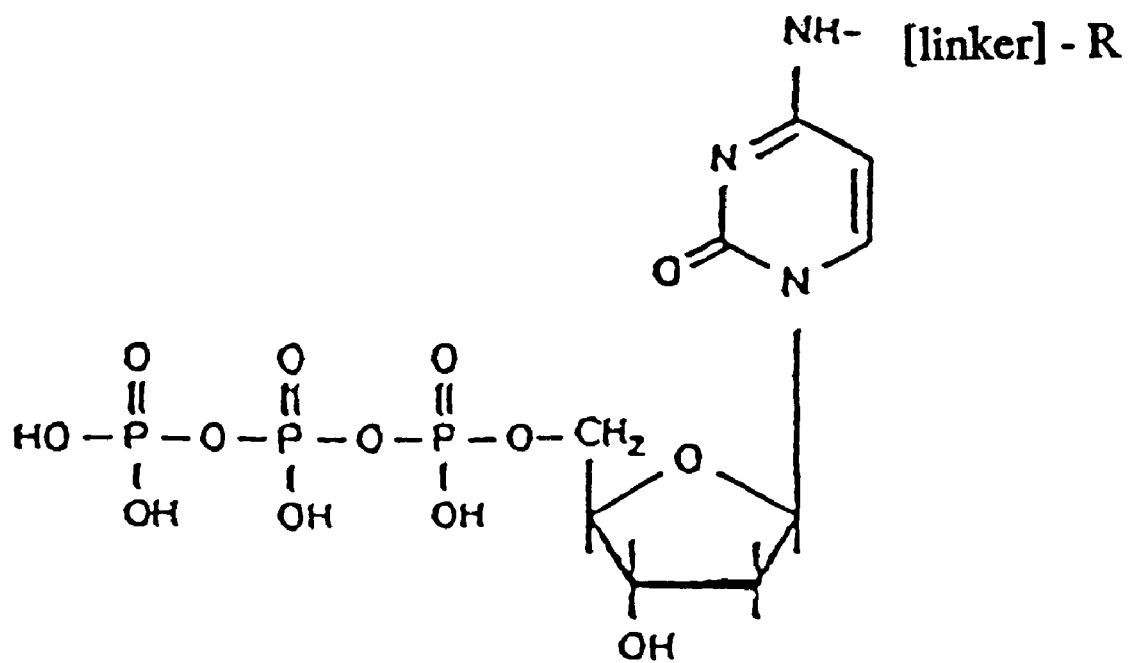

FIG. 1F  R = fluorescein
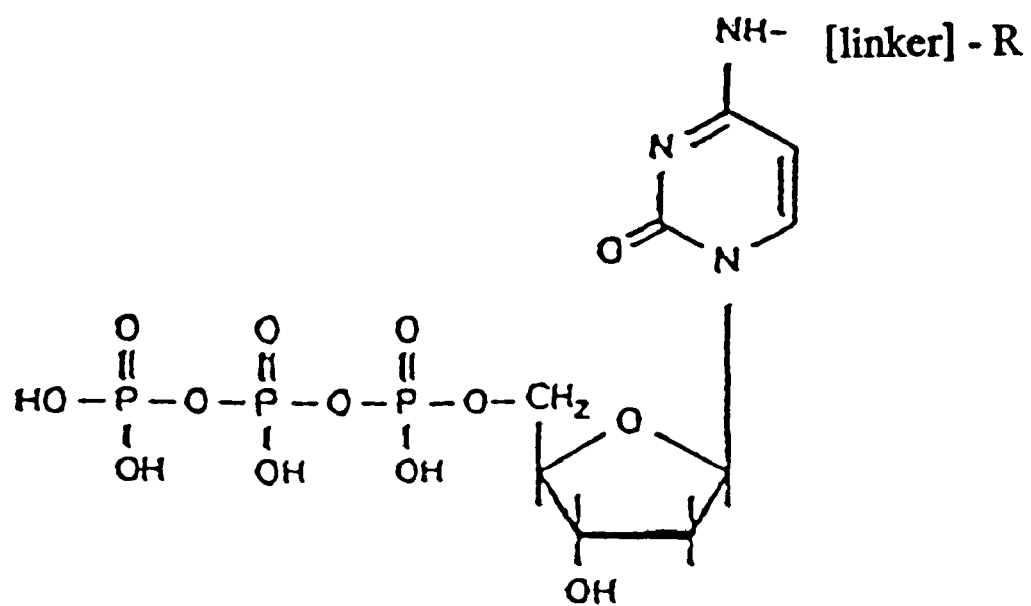

D.

To the L412M-DNA polymerase already present, add fluorophore-labeled dNTPs and, perhaps, accessory proteins.

complementary fluorophore-labeled DNA

E.

+ L412M DNA polymerase digestion by exonuclease fluorophore dNTPs endonuclease

SEQUENCE LISTING

```
<160> NUMBER OF SEQ ID NOS: 4

<210> SEQ ID NO 1
<211> LENGTH: 2694 base pairs
<212> TYPE: DNA
<213> ORGANISM: T2 bacteriophage
<300> PUBLICATION INFORMATION:
<301> AUTHORS: Goodman, Myron F.
      Reha-Krantz, Linda J.
<310> PATENT DOCUMENT NUMBER: US 5,660,980
<311> PATENT FILING DATE: 1995-06-06
<312> PUBLICATION DATE: 1997-08-26

<400> SEQUENCE: 1 atg aaa gaa ttt tat atc tct atc gaa aca gtc gga aat aat att           45
Met Lys Glu Phe Tyr Ile Ser Ile Glu Thr Val Gly Asn Asn Ile
                 5                  10                  15 att gaa cgt tat att gat gaa aac gga aag gaa cgt act cgt gaa           90
Ile Glu Arg Tyr Ile Asp Glu Asn Gly Lys Glu Arg Thr Arg Glu
                20                  25                  30 gta gaa tat ctt ccg act atg ttt agg cat tgt aag gaa gag tca          135
Val Glu Tyr Leu Pro Thr Met Phe Arg His Cys Lys Glu Glu Ser
                35                  40                  45 aaa tac aaa gac atc tat ggt aaa aac tgt gct cct caa aaa ttt          180
Lys Tyr Lys Asp Ile Tyr Gly Lys Asn Cys Ala Pro Gln Lys Phe
                50                  55                  60 cca tca atg aaa gat gct cga gat tgg atg aag cga atg gaa gac          225
Pro Ser Met Lys Asp Ala Arg Asp Trp Met Lys Arg Met Glu Asp
                65                  70                  75 atc ggt ctc gaa gct ctc ggt atg aac gat ttt aaa ctc gct tat          270
Ile Gly Leu Glu Ala Leu Gly Met Asn Asp Phe Lys Leu Ala Tyr
                80                  85                  90 atc agt gat acg tat ggt tca gaa att gtt tat gac cga aaa ttt          315
Ile Ser Asp Thr Tyr Gly Ser Glu Ile Val Tyr Asp Arg Lys Phe
                95                 100                 105 gtt cgt gta gct aac tgt gac att gag gtt act ggt gat aaa ttt          360
Val Arg Val Ala Asn Cys Asp Ile Glu Val Thr Gly Asp Lys Phe
               110                 115                 120 cct gac cca atg aaa gca gaa tat gaa att gat gct atc act cat          405
Pro Asp Pro Met Lys Ala Glu Tyr Glu Ile Asp Ala Ile Thr His
               125                 130                 135 tat gat tca att gac gac cgt ttt tat gtt ttc gac ctt ttg aat          450
```

-continued

```
                Tyr Asp Ser Ile Asp Asp Arg Phe Tyr Val Phe Asp Leu Leu Asn
                                140                 145                 150 tca atg tac ggt tca gta tca aaa tgg gat gca aag tta gct gct           495
Ser Met Tyr Gly Ser Val Ser Lys Trp Asp Ala Lys Leu Ala Ala
                155                 160                 165 aag ctt gac tgt gaa ggt ggt gat gaa gtt cct caa gaa att ctt           540
Lys Leu Asp Cys Glu Gly Gly Asp Glu Val Pro Gln Glu Ile Leu
                170                 175                 180 gac cga gta att tat atg cca ttt gat aat gag cgt gat atg ctc           585
Asp Arg Val Ile Tyr Met Pro Phe Asp Asn Glu Arg Asp Met Leu
                185                 190                 195 atg gaa tat att aat ctc tgg gaa cag aaa cga cct gct att ttt           630
Met Glu Tyr Ile Asn Leu Trp Glu Gln Lys Arg Pro Ala Ile Phe
                200                 205                 210 act ggt tgg aat att gag ggg ttt gac gtt ccg tat atc atg aat           675
Thr Gly Trp Asn Ile Glu Gly Phe Asp Val Pro Tyr Ile Met Asn
                215                 220                 225 cgc gtt aaa atg att ctg ggt gaa cgc agt atg aaa cgt ttc tct           720
Arg Val Lys Met Ile Leu Gly Glu Arg Ser Met Lys Arg Phe Ser
                230                 235                 240 cca atc ggt cgg gta aaa tct aaa cta att caa aat atg tac ggt           765
Pro Ile Gly Arg Val Lys Ser Lys Leu Ile Gln Asn Met Tyr Gly
                245                 250                 255 agc aaa gaa att tat tct att gat ggc gta tct att ctt gat tat           810
Ser Lys Glu Ile Tyr Ser Ile Asp Gly Val Ser Ile Leu Asp Tyr
                260                 265                 270 tta gat ttg tac aag aaa ttc gct ttt act aat ttg ccg tca ttc           855
Leu Asp Leu Tyr Lys Lys Phe Ala Phe Thr Asn Leu Pro Ser Phe
                275                 280                 285 tct ttg gaa tca gtt gct caa cat gaa acc aaa aaa ggt aaa tta           900
Ser Leu Glu Ser Val Ala Gln His Glu Thr Lys Lys Gly Lys Leu
                290                 295                 300 cca tac gac ggt cct att aat aaa ctt cgt gag act aat cat caa           945
Pro Tyr Asp Gly Pro Ile Asn Lys Leu Arg Glu Thr Asn His Gln
                305                 310                 315 cga tac att agt tat aac atc att gac gta gaa tca gtt caa gca           990
Arg Tyr Ile Ser Tyr Asn Ile Ile Asp Val Glu Ser Val Gln Ala
                320                 325                 330 att gat aaa att cgt ggg ttt atc gat cta gtt tta agt atg tct          1035
Ile Asp Lys Ile Arg Gly Phe Ile Asp Leu Val Leu Ser Met Ser
                335                 340                 345 tat tat gct aaa atg cct ttt tct ggt gta atg agt cct att aaa          1080
Tyr Tyr Ala Lys Met Pro Phe Ser Gly Val Met Ser Pro Ile Lys
                350                 355                 360 act tgg gat gct att att ttt aac tca ttg aaa ggt gaa cac aag          1125
Thr Trp Asp Ala Ile Ile Phe Asn Ser Leu Lys Gly Glu His Lys
                365                 370                 375 gtt att cct caa caa ggt tcg cac gtt aaa cag agt ttt ccg ggt          1170
Val Ile Pro Gln Gln Gly Ser His Val Lys Gln Ser Phe Pro Gly
                380                 385                 390 gca ttt gta ttt gaa cct aaa cca att gct cgt cga tac att atg          1215
Ala Phe Val Phe Glu Pro Lys Pro Ile Ala Arg Arg Tyr Ile Met
                395                 400                 405 agt ttt gac ttg acg tct ctg tat ccg agc att att cgc cag gtt          1260
Ser Phe Asp Leu Thr Ser Leu Tyr Pro Ser Ile Ile Arg Gln Val
                410                 415                 420 aac att agt cct gaa act att cgt ggt cag ttt aaa gtt cat cca          1305
Asn Ile Ser Pro Glu Thr Ile Arg Gly Gln Phe Lys Val His Pro
                425                 430                 435 att cat gaa tat atc gca gga aca gct cct aaa cca agt gat gaa          1350
```

```
Ile His Glu Tyr Ile Ala Gly Thr Ala Pro Lys Pro Ser Asp Glu
            440                 445                 450 tat tct tgt tct ccg aat gga tgg atg tat gat aag cat caa gaa     1395
Tyr Ser Cys Ser Pro Asn Gly Trp Met Tyr Asp Lys His Gln Glu
            455                 460                 465 ggt atc att cca aag gaa atc gct aaa gta ttt ttc cag cgt aaa     1440
Gly Ile Ile Pro Lys Glu Ile Ala Lys Val Phe Phe Gln Arg Lys
            470                 475                 480 gat tgg aaa aag aaa atg ttc gct gaa gaa atg aat gcc gaa gct     1485
Asp Trp Lys Lys Lys Met Phe Ala Glu Glu Met Asn Ala Glu Ala
            485                 490                 495 att aaa aag att att atg aaa ggc gca ggg tct tgt tca act aaa     1530
Ile Lys Lys Ile Ile Met Lys Gly Ala Gly Ser Cys Ser Thr Lys
            500                 505                 510 cca gaa gtt gaa cga tat gtt aag ttc act gat gat ttc tta aat     1575
Pro Glu Val Glu Arg Tyr Val Lys Phe Thr Asp Asp Phe Leu Asn
            515                 520                 525 gaa cta tcg aat tat act gaa tct gtt ctt aat agt ctg att gaa     1620
Glu Leu Ser Asn Tyr Thr Glu Ser Val Leu Asn Ser Leu Ile Glu
            530                 535                 540 gaa tgt gaa aaa gca gct aca ctt gct aat aca aat cag ctg aac     1665
Glu Cys Glu Lys Ala Ala Thr Leu Ala Asn Thr Asn Gln Leu Asn
            545                 550                 555 cgt aaa att ctt att aac agt ctt tat ggt gct ctt ggt aat att     1710
Arg Lys Ile Leu Ile Asn Ser Leu Tyr Gly Ala Leu Gly Asn Ile
            560                 565                 570 cat ttc cgt tac tat gat tta cga aat gct act gct atc aca att     1755
His Phe Arg Tyr Tyr Asp Leu Arg Asn Ala Thr Ala Ile Thr Ile
            575                 580                 585 ttt ggt caa gtt ggt att cag tgg att gct cgt aaa att aat gaa     1800
Phe Gly Gln Val Gly Ile Gln Trp Ile Ala Arg Lys Ile Asn Glu
            590                 595                 600 tat ctg aat aaa gta tgc gga act aat gat gaa gat ttc atc gca     1845
Tyr Leu Asn Lys Val Cys Gly Thr Asn Asp Glu Asp Phe Ile Ala
            605                 610                 615 gca ggt gat act gat tcg gta tat gtt tgt gta gat aaa gtt att     1890
Ala Gly Asp Thr Asp Ser Val Tyr Val Cys Val Asp Lys Val Ile
            620                 625                 630 gaa aaa gtt ggt ctt gac cga ttc aaa gag cag aac gat ttg gtt     1935
Glu Lys Val Gly Leu Asp Arg Phe Lys Glu Gln Asn Asp Leu Val
            635                 640                 645 gaa ttc atg aat cag ttt ggt aag aaa aag atg gaa cct atg att     1980
Glu Phe Met Asn Gln Phe Gly Lys Lys Lys Met Glu Pro Met Ile
            650                 655                 660 gat gtt gca tat cgt gag tta tgt gat tat atg aat aac cgc gag     2025
Asp Val Ala Tyr Arg Glu Leu Cys Asp Tyr Met Asn Asn Arg Glu
            665                 670                 675 cat ctg atg cat atg gac cgt gaa gct att tct tgc cct ccg ctt     2070
His Leu Met His Met Asp Arg Glu Ala Ile Ser Cys Pro Pro Leu
            680                 685                 690 ggt tca aag ggt gtt ggt gga ttt tgg aaa gcg aaa aaa cgt tat     2115
Gly Ser Lys Gly Val Gly Gly Phe Trp Lys Ala Lys Lys Arg Tyr
            695                 700                 705 gct ctg aac gtt tat gat atg gaa gat aag cga ttt gct gaa ccg     2160
Ala Leu Asn Val Tyr Asp Met Glu Asp Lys Arg Phe Ala Glu Pro
            710                 715                 720 cat cta aaa atc atg ggt atg gaa act cag cag agt tca aca cca     2205
His Leu Lys Ile Met Gly Met Glu Thr Gln Gln Ser Ser Thr Pro
            725                 730                 735 aaa gca gtg caa gaa gca ctc gaa gaa agt att cgt cgt att ctt     2250
```

| | | | | | | | | | | | | |
|---|---|---|---|---|---|---|---|---|---|---|---|---|
|Lys|Ala|Val|Gln|Glu|Ala|Leu|Glu|Glu|Ser|Ile|Arg|Arg|Ile|Leu|
| | | |740| | | | |745| | | | |750|

```
cag gaa ggc gaa gag tct gtc caa gaa tat tac aag aac ttc gag      2295
Gln Glu Gly Glu Glu Ser Val Gln Glu Tyr Tyr Lys Asn Phe Glu
            755                 760                 765 aaa gaa tat cgt caa ctt gac tat aaa gtt att gct gaa gta aaa      2340
Lys Glu Tyr Arg Gln Leu Asp Tyr Lys Val Ile Ala Glu Val Lys
            770                 775                 780 act gcg aac gat ata gcg aaa tat gat gat aaa ggt tgg cca gga      2385
Thr Ala Asn Asp Ile Ala Lys Tyr Asp Asp Lys Gly Trp Pro Gly
            795                 790                 795 ttt aaa tgt ccg ttc cat att cgt ggt gtg cta act tat cgt cga      2430
Phe Lys Cys Pro Phe His Ile Arg Gly Val Leu Thr Tyr Arg Arg
            800                 805                 810 gct gtt agt ggt ctg ggt gta gct cca att ttg gat gga aat aaa      2475
Ala Val Ser Gly Leu Gly Val Ala Pro Ile Leu Asp Gly Asn Lys
            815                 820                 825 gta atg gtt ctt cca tta cgt gaa gga aat ccg ttt ggt gat aag      2520
Val Met Val Leu Pro Leu Arg Glu Gly Asn Pro Phe Gly Asp Lys
            830                 835                 840 tgc att gct tgg cca tcg ggt aca gaa ctt cca aaa gaa att cgt      2565
Cys Ile Ala Trp Pro Ser Gly Thr Glu Leu Pro Lys Glu Ile Arg
            845                 850                 855 tct gat gta cta tct tgg att gac tac tca act ttg ttc caa aaa      2610
Ser Asp Val Leu Ser Trp Ile Asp Tyr Ser Thr Leu Phe Gln Lys
            860                 865                 870 tcg ttt gtt aaa ccg ctt gcg ggt atg tgt gaa tcg gca ggt atg      2655
Ser Phe Val Lys Pro Leu Ala Gly Met Cys Glu Ser Ala Gly Met
            875                 880                 885 gac tat gag gaa aaa gct tcg tta gac ttc ctg ttt ggc              2694
Asp Tyr Glu Glu Lys Ala Ser Leu Asp Phe Leu Phe Gly
            890                 895     898
```

<210> SEQ ID NO 2
<211> LENGTH: 898 amino acids
<212> TYPE: PRT
<213> ORGANISM: T2 bacteriophage
<300> PUBLICATION INFORMATION:
<301> AUTHORS: Goodman, Myron F.
      Reha-Krantz, Linda J.
<310> PATENT DOCUMENT NUMBER: US 5,660,980
<311> PATENT FILING DATE: 1995-06-06
<312> PUBLICATION DATE: 1997-08-26

<400> SEQUENCE: 2

```
Met Lys Glu Phe Tyr Ile Ser Ile Glu Thr Val Gly Asn Asn Ile
            5                   10                  15

Ile Glu Arg Tyr Ile Asp Glu Asn Gly Lys Glu Arg Thr Arg Glu
            20                  25                  30

Val Glu Tyr Leu Pro Thr Met Phe Arg His Cys Lys Glu Glu Ser
            35                  40                  45

Lys Tyr Lys Asp Ile Tyr Gly Lys Asn Cys Ala Pro Gln Lys Phe
            50                  55                  60

Pro Ser Met Lys Asp Ala Arg Asp Trp Met Lys Arg Met Glu Asp
            65                  70                  75

Ile Gly Leu Glu Ala Leu Gly Met Asn Asp Phe Lys Leu Ala Tyr
            80                  85                  90

Ile Ser Asp Thr Tyr Gly Ser Glu Ile Val Tyr Asp Arg Lys Phe
            95                  100                 105

Val Arg Val Ala Asn Cys Asp Ile Glu Val Thr Gly Asp Lys Phe
            110                 115                 120
```

```
Pro Asp Pro Met Lys Ala Glu Tyr Glu Ile Asp Ala Ile Thr His
            125                 130                 135
Tyr Asp Ser Ile Asp Asp Arg Phe Tyr Val Phe Asp Leu Leu Asn
            140                 145                 150
Ser Met Tyr Gly Ser Val Ser Lys Trp Asp Ala Lys Leu Ala Ala
            155                 160                 165
Lys Leu Asp Cys Glu Gly Gly Asp Glu Val Pro Gln Glu Ile Leu
            170                 175                 180
Asp Arg Val Ile Tyr Met Pro Phe Asp Asn Glu Arg Asp Met Leu
            185                 190                 195
Met Glu Tyr Ile Asn Leu Trp Glu Gln Lys Arg Pro Ala Ile Phe
            200                 205                 210
Thr Gly Trp Asn Ile Glu Gly Phe Asp Val Pro Tyr Ile Met Asn
            215                 220                 225
Arg Val Lys Met Ile Leu Gly Glu Arg Ser Met Lys Arg Phe Ser
            230                 235                 240
Pro Ile Gly Arg Val Lys Ser Lys Leu Ile Gln Asn Met Tyr Gly
            245                 250                 255
Ser Lys Glu Ile Tyr Ser Ile Asp Gly Val Ser Ile Leu Asp Tyr
            260                 265                 270
Leu Asp Leu Tyr Lys Lys Phe Ala Phe Thr Asn Leu Pro Ser Phe
            275                 280                 285
Ser Leu Glu Ser Val Ala Gln His Glu Thr Lys Lys Gly Lys Leu
            290                 295                 300
Pro Tyr Asp Gly Pro Ile Asn Lys Leu Arg Glu Thr Asn His Gln
            305                 310                 315
Arg Tyr Ile Ser Tyr Asn Ile Ile Asp Val Glu Ser Val Gln Ala
            320                 325                 330
Ile Asp Lys Ile Arg Gly Phe Ile Asp Leu Val Leu Ser Met Ser
            335                 340                 345
Tyr Tyr Ala Lys Met Pro Phe Ser Gly Val Met Ser Pro Ile Lys
            350                 355                 360
Thr Trp Asp Ala Ile Ile Phe Asn Ser Leu Lys Gly Glu His Lys
            365                 370                 375
Val Ile Pro Gln Gln Gly Ser His Val Lys Gln Ser Phe Pro Gly
            380                 385                 390
Ala Phe Val Phe Glu Pro Lys Pro Ile Ala Arg Arg Tyr Ile Met
            395                 400                 405
Ser Phe Asp Leu Thr Ser Leu Tyr Pro Ser Ile Ile Arg Gln Val
            410                 415                 420
Asn Ile Ser Pro Glu Thr Ile Arg Gly Gln Phe Lys Val His Pro
            425                 430                 435
Ile His Glu Tyr Ile Ala Gly Thr Ala Pro Lys Pro Ser Asp Glu
            440                 445                 450
Tyr Ser Cys Ser Pro Asn Gly Trp Met Tyr Asp Lys His Gln Glu
            455                 460                 465
Gly Ile Ile Pro Lys Glu Ile Ala Lys Val Phe Phe Gln Arg Lys
            470                 475                 480
Asp Trp Lys Lys Lys Met Phe Ala Glu Glu Met Asn Ala Glu Ala
            485                 490                 495
Ile Lys Lys Ile Ile Met Lys Gly Ala Gly Ser Cys Ser Thr Lys
            500                 505                 510
Pro Glu Val Glu Arg Tyr Val Lys Phe Thr Asp Asp Phe Leu Asn
```

```
                        515                 520                 525
Glu Leu Ser Asn Tyr Thr Glu Ser Val Leu Asn Ser Leu Ile Glu
                    530                 535                 540
Glu Cys Glu Lys Ala Ala Thr Leu Ala Asn Thr Asn Gln Leu Asn
                545                 550                 555
Arg Lys Ile Leu Ile Asn Ser Leu Tyr Gly Ala Leu Gly Asn Ile
            560                 565                 570
His Phe Arg Tyr Tyr Asp Leu Arg Asn Ala Thr Ala Ile Thr Ile
        575                 580                 585
Phe Gly Gln Val Gly Ile Gln Trp Ile Ala Arg Lys Ile Asn Glu
    590                 595                 600
Tyr Leu Asn Lys Val Cys Gly Thr Asn Asp Glu Asp Phe Ile Ala
605                 610                 615
Ala Gly Asp Thr Asp Ser Val Tyr Val Cys Val Asp Lys Val Ile
                620                 625                 630
Glu Lys Val Gly Leu Asp Arg Phe Lys Glu Gln Asn Asp Leu Val
            635                 640                 645
Glu Phe Met Asn Gln Phe Gly Lys Lys Met Glu Pro Met Ile
        650                 655                 660
Asp Val Ala Tyr Arg Glu Leu Cys Asp Tyr Met Asn Asn Arg Glu
    665                 670                 675
His Leu Met His Met Asp Arg Glu Ala Ile Ser Cys Pro Pro Leu
680                 685                 690
Gly Ser Lys Gly Val Gly Gly Phe Trp Lys Ala Lys Lys Arg Tyr
                695                 700                 705
Ala Leu Asn Val Tyr Asp Met Glu Asp Lys Arg Phe Ala Glu Pro
            710                 715                 720
His Leu Lys Ile Met Gly Met Glu Thr Gln Gln Ser Ser Thr Pro
        725                 730                 735
Lys Ala Val Gln Glu Ala Leu Glu Glu Ser Ile Arg Arg Ile Leu
    740                 745                 750
Gln Glu Gly Glu Glu Ser Val Gln Glu Tyr Tyr Lys Asn Phe Glu
755                 760                 765
Lys Glu Tyr Arg Gln Leu Asp Tyr Lys Val Ile Ala Glu Val Lys
                770                 775                 780
Thr Ala Asn Asp Ile Ala Lys Tyr Asp Asp Lys Gly Trp Pro Gly
            785                 790                 795
Phe Lys Cys Pro Phe His Ile Arg Gly Val Leu Thr Tyr Arg Arg
        800                 805                 810
Ala Val Ser Gly Leu Gly Val Ala Pro Ile Leu Asp Gly Asn Lys
    815                 820                 825
Val Met Val Leu Pro Leu Arg Glu Gly Asn Pro Phe Gly Asp Lys
830                 835                 840
Cys Ile Ala Trp Pro Ser Gly Thr Glu Leu Pro Lys Glu Ile Arg
                845                 850                 855
Ser Asp Val Leu Ser Trp Ile Asp Tyr Ser Thr Leu Phe Gln Lys
            860                 865                 870
Ser Phe Val Lys Pro Leu Ala Gly Met Cys Glu Ser Ala Gly Met
        875                 880                 885
Asp Tyr Glu Glu Lys Ala Ser Leu Asp Phe Leu Phe Gly
    890                 895             898

<210> SEQ ID NO 3
<211> LENGTH: 2694 base pairs
```

```
<212> TYPE: DNA
<213> ORGANISM: T4 bacteriophage
<300> PUBLICATION INFORMATION:
<301> AUTHORS: Goodman, Myron F.
              Reha-Krantz, Linda J.
<310> PATENT DOCUMENT NUMBER: US 5,660,980
<311> PATENT FILING DATE: 1995-06-06
<312> PUBLICATION DATE: 1997-08-26

<400> SEQUENCE: 3
```

| | | | | | | | | | | | | | | | |
|---|---|---|---|---|---|---|---|---|---|---|---|---|---|---|---|
| atg | aaa | gaa | ttt | tat | atc | tct | att | gaa | aca | gtc | gga | aat | aac | att | 45 |
| Met | Lys | Glu | Phe | Tyr | Ile | Ser | Ile | Glu | Thr | Val | Gly | Asn | Asn | Ile | |
| | | | | 5 | | | | | 10 | | | | | 15 | |
| gtt | gaa | cgt | tat | att | gat | gaa | aat | gga | aag | gaa | cgt | acc | cgt | gaa | 90 |
| Val | Glu | Arg | Tyr | Ile | Asp | Glu | Asn | Gly | Lys | Glu | Arg | Thr | Arg | Glu | |
| | | | | 20 | | | | | 25 | | | | | 30 | |
| gta | gaa | tat | ctt | cca | act | atg | ttt | agg | cat | tgt | aag | gaa | gag | tca | 135 |
| Val | Glu | Tyr | Leu | Pro | Thr | Met | Phe | Arg | His | Cys | Lys | Glu | Glu | Ser | |
| | | | | 35 | | | | | 40 | | | | | 45 | |
| aaa | tac | aaa | gac | atc | tat | ggt | aaa | aac | tgc | gct | cct | caa | aaa | ttt | 180 |
| Lys | Tyr | Lys | Asp | Ile | Tyr | Gly | Lys | Asn | Cys | Ala | Pro | Gln | Lys | Phe | |
| | | | | 50 | | | | | 55 | | | | | 60 | |
| cca | tca | atg | aaa | gat | gct | cga | gat | tgg | atg | aag | cga | atg | gaa | gac | 225 |
| Pro | Ser | Met | Lys | Asp | Ala | Arg | Asp | Trp | Met | Lys | Arg | Met | Glu | Asp | |
| | | | | 65 | | | | | 70 | | | | | 75 | |
| atc | ggt | ctc | gaa | gct | ctc | ggt | atg | aac | gat | ttt | aaa | ctc | gct | tat | 270 |
| Ile | Gly | Leu | Glu | Ala | Leu | Gly | Met | Asn | Asp | Phe | Lys | Leu | Ala | Tyr | |
| | | | | 80 | | | | | 85 | | | | | 90 | |
| ata | agt | gat | aca | tat | ggt | tca | gaa | att | gtt | tat | gac | cga | aaa | ttt | 315 |
| Ile | Ser | Asp | Thr | Tyr | Gly | Ser | Glu | Ile | Val | Tyr | Asp | Arg | Lys | Phe | |
| | | | | 95 | | | | | 100 | | | | | 105 | |
| gtt | cgt | gta | gct | aac | tgt | gac | att | gag | gtt | act | ggt | gat | aaa | ttt | 360 |
| Val | Arg | Val | Ala | Asn | Cys | Asp | Ile | Glu | Val | Thr | Gly | Asp | Lys | Phe | |
| | | | | 110 | | | | | 115 | | | | | 120 | |
| cct | gac | cca | atg | aaa | gca | gaa | tat | gaa | att | gat | gct | atc | act | cat | 405 |
| Pro | Asp | Pro | Met | Lys | Ala | Glu | Tyr | Glu | Ile | Asp | Ala | Ile | Thr | His | |
| | | | | 125 | | | | | 130 | | | | | 135 | |
| tac | gat | tca | att | gac | gat | cgt | ttt | tat | gtt | ttc | gac | ctt | ttg | aat | 450 |
| Tyr | Asp | Ser | Ile | Asp | Asp | Arg | Phe | Tyr | Val | Phe | Asp | Leu | Leu | Asn | |
| | | | | 140 | | | | | 145 | | | | | 150 | |
| tca | atg | tac | ggt | tca | gta | tca | aaa | tgg | gat | gca | aag | tta | gct | gct | 495 |
| Ser | Met | Tyr | Gly | Ser | Val | Ser | Lys | Trp | Asp | Ala | Lys | Leu | Ala | Ala | |
| | | | | 155 | | | | | 160 | | | | | 165 | |
| aag | ctt | gac | tgt | gaa | ggt | ggt | gat | gaa | gtt | cct | caa | gaa | att | ctt | 540 |
| Lys | Leu | Asp | Cys | Glu | Gly | Gly | Asp | Glu | Val | Pro | Gln | Glu | Ile | Leu | |
| | | | | 170 | | | | | 175 | | | | | 180 | |
| gac | cga | gta | att | tat | atg | cca | ttc | gat | aat | gag | cgt | gat | atg | ctc | 585 |
| Asp | Arg | Val | Ile | Tyr | Met | Pro | Phe | Asp | Asn | Glu | Arg | Asp | Met | Leu | |
| | | | | 185 | | | | | 190 | | | | | 195 | |
| atg | gaa | tat | atc | aat | ctt | tgg | gaa | cag | aaa | cga | cct | gct | att | ttt | 630 |
| Met | Glu | Tyr | Ile | Asn | Leu | Trp | Glu | Gln | Lys | Arg | Pro | Ala | Ile | Phe | |
| | | | | 200 | | | | | 205 | | | | | 210 | |
| act | ggt | tgg | aat | att | gag | ggg | ttt | gac | gtt | ccg | tat | atc | atg | aat | 675 |
| Thr | Gly | Trp | Asn | Ile | Glu | Gly | Phe | Asp | Val | Pro | Tyr | Ile | Met | Asn | |
| | | | | 215 | | | | | 220 | | | | | 225 | |
| cgt | gtt | aaa | atg | att | ctg | ggt | gaa | cgt | agt | atg | aaa | cgt | ttc | tct | 720 |
| Arg | Val | Lys | Met | Ile | Leu | Gly | Glu | Arg | Ser | Met | Lys | Arg | Phe | Ser | |
| | | | | 230 | | | | | 235 | | | | | 240 | |
| cca | atc | ggt | cgg | gta | aaa | tct | aaa | cta | att | caa | aat | atg | tac | ggt | 765 |
| Pro | Ile | Gly | Arg | Val | Lys | Ser | Lys | Leu | Ile | Gln | Asn | Met | Tyr | Gly | |
| | | | | 245 | | | | | 250 | | | | | 255 | |
| agc | aaa | gaa | att | tat | tct | att | gat | ggc | gta | tct | att | ctt | gat | tat | 810 |

|   |   |   |   |   |   |   |   |   |   |   |   |   |
|---|---|---|---|---|---|---|---|---|---|---|---|---|
| Ser | Lys | Glu | Ile | Tyr | Ser | Ile | Asp | Gly | Val | Ser | Ile | Leu | Asp | Tyr |
|   |   |   | 260 |   |   |   | 265 |   |   |   | 270 |

```
tta gat ttg tac aag aaa ttc gct ttt act aat ttg ccg tca ttc       855
Leu Asp Leu Tyr Lys Lys Phe Ala Phe Thr Asn Leu Pro Ser Phe
            275                 280                 285 tct ttg gaa tca gtt gct caa cat gaa acc aaa aaa ggt aaa tta       900
Ser Leu Glu Ser Val Ala Gln His Glu Thr Lys Lys Gly Lys Leu
                290                 295                 300 cca tac gac ggt cct att aat aaa ctt cgt gag act aat cat caa       945
Pro Tyr Asp Gly Pro Ile Asn Lys Leu Arg Glu Thr Asn His Gln
                305                 310                 315 cga tac att agt tat aac atc att gac gta gaa tca gtt caa gca       990
Arg Tyr Ile Ser Tyr Asn Ile Ile Asp Val Glu Ser Val Gln Ala
                320                 325                 330 atc gat aaa att cgt ggg ttt atc gat cta gtt tta agt atg tct      1035
Ile Asp Lys Ile Arg Gly Phe Ile Asp Leu Val Leu Ser Met Ser
                335                 340                 345 tat tac gct aaa atg cct ttt tct ggt gta atg agt cct att aaa      1080
Tyr Tyr Ala Lys Met Pro Phe Ser Gly Val Met Ser Pro Ile Lys
                350                 355                 360 act tgg gat gct att att ttt aac tca ttg aaa ggt gaa cat aag      1125
Thr Trp Asp Ala Ile Ile Phe Asn Ser Leu Lys Gly Glu His Lys
                365                 370                 375 gtt att cct caa caa ggt tcg cac gtt aaa cag agt ttt ccg ggt      1170
Val Ile Pro Gln Gln Gly Ser His Val Lys Gln Ser Phe Pro Gly
                380                 385                 390 gca ttt gtg ttt gaa cct aaa cca att gca cgt cga tac att atg      1215
Ala Phe Val Phe Glu Pro Lys Pro Ile Ala Arg Arg Tyr Ile Met
                395                 400                 405 agt ttt gac ttg acg tct ctg tat ccg agc att att cgc cag gtt      1260
Ser Phe Asp Leu Thr Ser Leu Tyr Pro Ser Ile Ile Arg Gln Val
                410                 415                 420 aac att agt cct gaa act att cgt ggt cag ttt aaa gtt cat cca      1305
Asn Ile Ser Pro Glu Thr Ile Arg Gly Gln Phe Lys Val His Pro
                425                 430                 435 att cat gaa tat atc gca gga aca gct cct aaa ccg agt gat gaa      1350
Ile His Glu Tyr Ile Ala Gly Thr Ala Pro Lys Pro Ser Asp Glu
                440                 445                 450 tat tct tgt tct ccg aat gga tgg atg tat gat aaa cat caa gaa      1395
Tyr Ser Cys Ser Pro Asn Gly Trp Met Tyr Asp Lys His Gln Glu
                455                 460                 465 ggt atc att cca aag gaa atc gct aaa gta ttt ttc cag cgt aaa      1440
Gly Ile Ile Pro Lys Glu Ile Ala Lys Val Phe Phe Gln Arg Lys
                470                 475                 480 gac tgg aaa aag aaa atg ttc gct gaa gaa atg aat gcc gaa gct      1485
Asp Trp Lys Lys Lys Met Phe Ala Glu Glu Met Asn Ala Glu Ala
                485                 490                 495 att aaa aag att att atg aaa ggc gca ggg tct tgt tca act aaa      1530
Ile Lys Lys Ile Ile Met Lys Gly Ala Gly Ser Cys Ser Thr Lys
                500                 505                 510 cca gaa gtt gaa cga tat gtt aag ttc agt gat gat ttc tta aat      1575
Pro Glu Val Glu Arg Tyr Val Lys Phe Ser Asp Asp Phe Leu Asn
                515                 520                 525 gaa cta tcg aat tac acc gaa tct gtt ctc aat agt ctg att gaa      1620
Glu Leu Ser Asn Tyr Thr Glu Ser Val Leu Asn Ser Leu Ile Glu
                530                 535                 540 gaa tgt gaa aaa gca gct aca ctt gct aat aca aat cag ctg aac      1665
Glu Cys Glu Lys Ala Ala Thr Leu Ala Asn Thr Asn Gln Leu Asn
                545                 550                 555 cgt aaa att ctc att aac agt ctt tat ggt gct ctt ggt aat att      1710
```

-continued

```
Arg Lys Ile Leu Ile Asn Ser Leu Tyr Gly Ala Leu Gly Asn Ile
            560                 565                 570 cat ttc cgt tac tat gat ttg cga aat gct act gct atc aca att          1755
His Phe Arg Tyr Tyr Asp Leu Arg Asn Ala Thr Ala Ile Thr Ile
            575                 580                 585 ttc ggc caa gtc ggt att cag tgg att gct cgt aaa att aat gaa          1800
Phe Gly Gln Val Gly Ile Gln Trp Ile Ala Arg Lys Ile Asn Glu
            590                 595                 600 tat ctg aat aaa gta tgc gga act aat gat gaa gat ttc att gca          1845
Tyr Leu Asn Lys Val Cys Gly Thr Asn Asp Glu Asp Phe Ile Ala
            605                 610                 615 gca ggt gat act gat tcg gta tat gtt tgc gta gat aaa gtt att          1890
Ala Gly Asp Thr Asp Ser Val Tyr Val Cys Val Asp Lys Val Ile
            620                 625                 630 gaa aaa gtt ggt ctt gac cga ttc aaa gag cag aac gat ttg gtt          1935
Glu Lys Val Gly Leu Asp Arg Phe Lys Glu Gln Asn Asp Leu Val
            635                 640                 645 gaa ttc atg aat cag ttc ggt aag aaa aag atg gaa cct atg att          1980
Glu Phe Met Asn Gln Phe Gly Lys Lys Lys Met Glu Pro Met Ile
            650                 655                 660 gat gtt gca tat cgt gag tta tgt gat tat atg aat aac cgc gag          2025
Asp Val Ala Tyr Arg Glu Leu Cys Asp Tyr Met Asn Asn Arg Glu
            665                 670                 675 cat ctg atg cat atg gac cgt gaa gct att tct tgc cct ccg ctt          2070
His Leu Met His Met Asp Arg Glu Ala Ile Ser Cys Pro Pro Leu
            680                 685                 690 ggt tca aag ggc gtt ggt gga ttt tgg aaa gcg aaa aag cgt tat          2115
Gly Ser Lys Gly Val Gly Gly Phe Trp Lys Ala Lys Lys Arg Tyr
            695                 700                 705 gct ctg aac gtt tat gat atg gaa gat aag cga ttt gct gaa ccg          2160
Ala Leu Asn Val Tyr Asp Met Glu Asp Lys Arg Phe Ala Glu Pro
            710                 715                 720 cat cta aaa atc atg ggt atg gaa act cag cag agt tca aca cca          2205
His Leu Lys Ile Met Gly Met Glu Thr Gln Gln Ser Ser Thr Pro
            725                 730                 735 aaa gca gtg caa gaa gct ctc gaa gaa agt att cgt cgt att ctt          2250
Lys Ala Val Gln Glu Ala Leu Glu Glu Ser Ile Arg Arg Ile Leu
            740                 745                 750 cag gaa ggt gaa gag tct gtc caa gaa tac tac aag aac ttc gag          2295
Gln Glu Gly Glu Glu Ser Val Gln Glu Tyr Tyr Lys Asn Phe Glu
            755                 760                 765 aaa gaa tat cgt caa ctt gac tat aaa gtt att gct gaa gta aaa          2340
Lys Glu Tyr Arg Gln Leu Asp Tyr Lys Val Ile Ala Glu Val Lys
            770                 775                 780 act gcg aac gat ata gcg aaa tat gat gat aaa ggt tgg cca gga          2385
Thr Ala Asn Asp Ile Ala Lys Tyr Asp Asp Lys Gly Trp Pro Gly
            785                 790                 795 ttt aaa tgc ccg ttc cat att cgt ggt gtg cta act tat cgt cga          2430
Phe Lys Cys Pro Phe His Ile Arg Gly Val Leu Thr Tyr Arg Arg
            800                 805                 810 gct gtt agc ggt tta ggt gta gct cca att ttg gat gga aat aaa          2475
Ala Val Ser Gly Leu Gly Val Ala Pro Ile Leu Asp Gly Asn Lys
            815                 820                 825 gta atg gtt ctt cca tta cgt gaa gga aat cca ttt ggt gac aag          2520
Val Met Val Leu Pro Leu Arg Glu Gly Asn Pro Phe Gly Asp Lys
            830                 835                 840 tgc att gct tgg cca tcg ggt aca gaa ctt cca aaa gaa att cgt          2565
Cys Ile Ala Trp Pro Ser Gly Thr Glu Leu Pro Lys Glu Ile Arg
            845                 850                 855 tct gat gtg cta tct tgg att gac cac tca act ttg ttc caa aaa          2610
```

| | | | | | | | | | | | | |
|---|---|---|---|---|---|---|---|---|---|---|---|---|
|Ser|Asp|Val|Leu|Ser|Trp|Ile|Asp|His|Ser|Thr|Leu|Phe|Gln|Lys|
| | | |860| | | |865| | | |870| |

```
tcg ttt gtt aaa ccg ctt gcg ggt atg tgt gaa tcg gct ggc atg          2655
Ser Phe Val Lys Pro Leu Ala Gly Met Cys Glu Ser Ala Gly Met
            875                 880                 885 gac tat gaa gaa aaa gct tcg tta gac ttc ctg ttt ggc                  2694
Asp Tyr Glu Glu Lys Ala Ser Leu Asp Phe Leu Phe Gly
            890                 895     898

<210> SEQ ID NO 4
<211> LENGTH: 898 amino acids
<212> TYPE: PRT
<213> ORGANISM: T4 bacteriophage
<300> PUBLICATION INFORMATION:
<301> AUTHORS: Goodman, Myron F.
              Reha-Krantz, Linda J.
<310> PATENT DOCUMENT NUMBER: US 5,660,980
<311> PATENT FILING DATE: 1995-06-06
<312> PUBLICATION DATE: 1997-08-26

<400> SEQUENCE: 4

Met Lys Glu Phe Tyr Ile Ser Ile Glu Thr Val Gly Asn Asn Ile
                  5                  10                  15

Val Glu Arg Tyr Ile Asp Glu Asn Gly Lys Glu Arg Thr Arg Glu
                 20                  25                  30

Val Glu Tyr Leu Pro Thr Met Phe Arg His Cys Lys Glu Glu Ser
                 35                  40                  45

Lys Tyr Lys Asp Ile Tyr Gly Lys Asn Cys Ala Pro Gln Lys Phe
                 50                  55                  60

Pro Ser Met Lys Asp Ala Arg Asp Trp Met Lys Arg Met Glu Asp
                 65                  70                  75

Ile Gly Leu Glu Ala Leu Gly Met Asn Asp Phe Lys Leu Ala Tyr
                 80                  85                  90

Ile Ser Asp Thr Tyr Gly Ser Glu Ile Val Tyr Asp Arg Lys Phe
                 95                 100                 105

Val Arg Val Ala Asn Cys Asp Ile Glu Val Thr Gly Asp Lys Phe
                110                 115                 120

Pro Asp Pro Met Lys Ala Glu Tyr Glu Ile Asp Ala Ile Thr His
                125                 130                 135

Tyr Asp Ser Ile Asp Asp Arg Phe Tyr Val Phe Asp Leu Leu Asn
                140                 145                 150

Ser Met Tyr Gly Ser Val Ser Lys Trp Asp Ala Lys Leu Ala Ala
                155                 160                 165

Lys Leu Asp Cys Glu Gly Gly Asp Glu Val Pro Gln Glu Ile Leu
                170                 175                 180

Asp Arg Val Ile Tyr Met Pro Phe Asp Asn Glu Arg Asp Met Leu
                185                 190                 195

Met Glu Tyr Ile Asn Leu Trp Glu Gln Lys Arg Pro Ala Ile Phe
                200                 205                 210

Thr Gly Trp Asn Ile Glu Gly Phe Asp Val Pro Tyr Ile Met Asn
                215                 220                 225

Arg Val Lys Met Ile Leu Gly Glu Arg Ser Met Lys Arg Phe Ser
                230                 235                 240

Pro Ile Gly Arg Val Lys Ser Lys Leu Ile Gln Asn Met Tyr Gly
                245                 250                 255

Ser Lys Glu Ile Tyr Ser Ile Asp Gly Val Ser Ile Leu Asp Tyr
                260                 265                 270

Leu Asp Leu Tyr Lys Lys Phe Ala Phe Thr Asn Leu Pro Ser Phe
```

```
                        275                 280                 285
Ser Leu Glu Ser Val Ala Gln His Glu Thr Lys Lys Gly Lys Leu
                290                 295                 300

Pro Tyr Asp Gly Pro Ile Asn Lys Leu Arg Glu Thr Asn His Gln
            305                 310                 315

Arg Tyr Ile Ser Tyr Asn Ile Ile Asp Val Glu Ser Val Gln Ala
        320                 325                 330

Ile Asp Lys Ile Arg Gly Phe Ile Asp Leu Val Leu Ser Met Ser
    335                 340                 345

Tyr Tyr Ala Lys Met Pro Phe Ser Gly Val Met Ser Pro Ile Lys
350                 355                 360

Thr Trp Asp Ala Ile Ile Phe Asn Ser Leu Lys Gly Glu His Lys
            365                 370                 375

Val Ile Pro Gln Gln Gly Ser His Val Lys Gln Ser Phe Pro Gly
        380                 385                 390

Ala Phe Val Phe Glu Pro Lys Pro Ile Ala Arg Arg Tyr Ile Met
    395                 400                 405

Ser Phe Asp Leu Thr Ser Leu Tyr Pro Ser Ile Ile Arg Gln Val
410                 415                 420

Asn Ile Ser Pro Glu Thr Ile Arg Gly Gln Phe Lys Val His Pro
            425                 430                 435

Ile His Glu Tyr Ile Ala Gly Thr Ala Pro Lys Pro Ser Asp Glu
        440                 445                 450

Tyr Ser Cys Ser Pro Asn Gly Trp Met Tyr Asp Lys His Gln Glu
    455                 460                 465

Gly Ile Ile Pro Lys Glu Ile Ala Lys Val Phe Phe Gln Arg Lys
470                 475                 480

Asp Trp Lys Lys Lys Met Phe Ala Glu Glu Met Asn Ala Glu Ala
            485                 490                 495

Ile Lys Lys Ile Ile Met Lys Gly Ala Gly Ser Cys Ser Thr Lys
        500                 505                 510

Pro Glu Val Glu Arg Tyr Val Lys Phe Ser Asp Asp Phe Leu Asn
    515                 520                 525

Glu Leu Ser Asn Tyr Thr Glu Ser Val Leu Asn Ser Leu Ile Glu
530                 535                 540

Glu Cys Glu Lys Ala Ala Thr Leu Ala Asn Thr Asn Gln Leu Asn
            545                 550                 555

Arg Lys Ile Leu Ile Asn Ser Leu Tyr Gly Ala Leu Gly Asn Ile
        560                 565                 570

His Phe Arg Tyr Tyr Asp Leu Arg Asn Ala Thr Ala Ile Thr Ile
    575                 580                 585

Phe Gly Gln Val Gly Ile Gln Trp Ile Ala Arg Lys Ile Asn Glu
590                 595                 600

Tyr Leu Asn Lys Val Cys Gly Thr Asn Asp Glu Asp Phe Ile Ala
            605                 610                 615

Ala Gly Asp Thr Asp Ser Val Tyr Val Cys Val Asp Lys Val Ile
        620                 625                 630

Glu Lys Val Gly Leu Asp Arg Phe Lys Glu Gln Asn Asp Leu Val
    635                 640                 645

Glu Phe Met Asn Gln Phe Gly Lys Lys Met Glu Pro Met Ile
650                 655                 660

Asp Val Ala Tyr Arg Glu Leu Cys Asp Tyr Met Asn Asn Arg Glu
            665                 670                 675
```

```
His Leu Met His Met Asp Arg Glu Ala Ile Ser Cys Pro Pro Leu
            680                 685              690

Gly Ser Lys Gly Val Gly Gly Phe Trp Lys Ala Lys Lys Arg Tyr
            695                 700              705

Ala Leu Asn Val Tyr Asp Met Glu Asp Lys Arg Phe Ala Glu Pro
            710                 715              720

His Leu Lys Ile Met Gly Met Glu Thr Gln Gln Ser Ser Thr Pro
            725                 730              735

Lys Ala Val Gln Glu Ala Leu Glu Glu Ser Ile Arg Arg Ile Leu
            740                 745              750

Gln Glu Gly Glu Glu Ser Val Gln Glu Tyr Tyr Lys Asn Phe Glu
            755                 760              765

Lys Glu Tyr Arg Gln Leu Asp Tyr Lys Val Ile Ala Glu Val Lys
            770                 775              780

Thr Ala Asn Asp Ile Ala Lys Tyr Asp Asp Lys Gly Trp Pro Gly
            785                 790              795

Phe Lys Cys Pro Phe His Ile Arg Gly Val Leu Thr Tyr Arg Arg
            800                 805              810

Ala Val Ser Gly Leu Gly Val Ala Pro Ile Leu Asp Gly Asn Lys
            815                 820              825

Val Met Val Leu Pro Leu Arg Glu Gly Asn Pro Phe Gly Asp Lys
            830                 835              840

Cys Ile Ala Trp Pro Ser Gly Thr Glu Leu Pro Lys Glu Ile Arg
            845                 850              855

Ser Asp Val Leu Ser Trp Ile Asp His Ser Thr Leu Phe Gln Lys
            860                 865              870

Ser Phe Val Lys Pro Leu Ala Gly Met Cys Glu Ser Ala Gly Met
            875                 880              885

Asp Tyr Glu Glu Lys Ala Ser Leu Asp Phe Leu Phe Gly
            890                 895         898
```

SYNTHESIS OF FLUOROPHORE-LABELED DNA

This application is a division of application Ser. No. 08/632,742, filed Apr. 15, 1996, now abandoned.

TECHNICAL FIELD OF THE INVENTION

The present invention relates generally to the fields of biology and chemistry. More particularly, the present invention is directed to methods for use in sequencing deoxyribonucleic acid (hereinafter referred to as "DNA") and for labeling DNA probes.

BACKGROUND OF THE INVENTION

Although a substantial amount of research has been directed to the development of sequencing methods, a limitation of current day techniques is that sequence information is obtained in units of only 400 to 600 nucleotides. For genome sequencing projects, such as sequencing the human genome, it would be inefficient to fit together such small units of sequence information. Longer units of sequence information would also be required in order to sequence through many repeated DNA sequences.

One proposed method to increase the length of sequence information is the single molecule sequencing method [U.S. Pat. No. 4,962,037; Jett, J. H., et al., *J. Biomolecular Structure & Dynamics*, 7:301–309 (1989); Ambrose, et al., *Ber. Bunseniges Phys. Chem.*, 97:1535 (1993)]. For the single molecule sequencing method, a DNA polymerase is used to synthesize a complementary DNA with fluorophore-labeled deoxynucleoside triphosphates (fluorophore dNTPs). Each of the four fluorophore dNTPs has a unique fluorophore tag that can be used to identify the nucleotide. A single fluorophore-labeled DNA is then immobilized in a flow cell and subjected to exonuclease digestion. A flow system carries each released fluorophore-labeled deoxynucleoside monophosphate (fluorophore dNMP) to a highly sensitive fluorescence detector capable of single molecule detection. The order of the fluorophore dNMPs detected gives the sequence. Because in vitro fluorophore-labeled DNA synthesized in this manner may be tens of thousands of nucleotides in length, this method will be useful in providing long sequence information.

The single molecule sequencing method has two primary enzymatic components. The first enzymatic component is employed in the synthesis of the complementary fluorophore-labeled DNA, synthesis being achieved by DNA polymerase-mediated incorporation of fluorophore-labeled nucleotides. The second enzymatic component is involved in digestion of the fluorophore-labeled DNA to release fluorophore dNMPs.

In principle, DNA polymerases from a variety of organisms would appear to have the potential to be used in in vitro reactions for the synthesis of complementary, fluorophore-labeled DNA. In practice, few DNA polymerases have been found to be suitable for this purpose. Synthesis of the complementary, fluorophore DNA requires first that the DNA polymerase have the ability to incorporate the fluorophore nucleotide. Second, the DNA polymerase must then be able to extend the fluorophore-labeled terminal nucleotide by addition of the next complementary fluorophore nucleotide. Incorporation of fluorophore nucleotides and extension of a fluorophore-labeled terminus are steps that are discriminated against by most DNA polymerases. A third requirement is that DNA replication must be accurate so that a faithful complementary fluorophore-labeled DNA is synthesized.

Methods for the synthesis of long fluorophore-labeled DNA can also be used to make shorter labeled DNAs, to be used as probes. DNA probes are used to identify chromosomes, locate genes and mRNA, etc. These methods can also be used to synthesize biotin-labeled DNA, DIG-labeled DNA, etc., which rely on the enzymatic incorporation into DNA of a labeled or modified nucleotide. "DIG" is the abbreviation of digoxigenin. For the biotin- and DIG-labeled DNAs, biotin- or DIG-labeled nucleotides are used; a fluorophore-dNTP is used for the synthesis of fluorophore-labeled DNA.

Another deficiency in current DNA sequencing methods is speed. The single molecule sequencing method has the potential to increase sequencing speed to 10 or more nucleotides per second [U.S. Pat. No. 4,962,037; Jett, J. H., et al., *J. Biomolecular Structure & Dynamics*, 7:301–309 (1989)]. Another method that has the potential to increase speed is mass spectrometry [Chen, C. H., et al., *SPEI* 2386:1322 (1995)]. Presently, a mass spectrometric method has been reported to sequence a 35-nucleotide oligomer in a few seconds. A limitation of mass spectrometry is that only short DNAs can be sequenced. Longer DNAs can be sequenced by mass spectrometry if the differences in mass between the four nucleotides can be increased. One way to increase differences in the mass of nucleotides is to use modified nucleotides, hence, synthesis of a complementary DNA with modified nucleotides may be the means to make mass spectrometry a useful sequencing method.

It is an object of the present invention to provide compositions and methods which do not suffer from all the drawbacks of the prior art.

SUMMARY OF THE INVENTION

In accordance with the present invention, there are provided improved DNA polymerases and methods for synthesizing DNA molecules with modified nucleotides using these improved DNA polymerases. These improved DNA polymerases have increased intrinsic processivity and increased ability to synthesize a complementary DNA (e.g., from a DNA template) using a wide variety of modified nucleotides. For example, these improved DNA polymerases can be novel native DNA polymerases with increased processivity compared to known DNA polymerases. The improved DNA polymerases can also be mutant DNA polymerases which possess increased intrinsic processivity compared to their native DNA polymerase counterparts. The resulting modified DNA products can be used in a variety of applications including, but not limited to, synthesis of DNA probes and DNA sequencing. In accordance with one aspect of the invention, there are provided novel enzymes which may be used as DNA sequencing polymerases. These enzymes result from genetic mutations of family B DNA polymerases. In a preferred embodiment, the methods use mutant bacteriophage T4 DNA polymerases which have increased ability to synthesize accurately short or long chains of complementary, modified, e.g., fluorophore-labeled DNA. In general, the mutant T4 DNA polymerases retain 3'→5' exonuclease activity; hence, reduction or elimination of 3'→5' exonuclease activity is not a prerequisite for efficient synthesis of a fluorophore-labeled complementary DNA. In fact, retention of 3'→5' exonuclease activity increases accuracy of DNA replication, because the exonuclease activity proofreads or edits the product of DNA replication.

BRIEF DESCRIPTION OF THE DRAWINGS

The invention may be better understood with reference to the accompanying drawings, in which:

FIGS. 1A–1F depict the structure of exemplary fluorophore nucleotides useful in the practice of the invention;

DETAILED DESCRIPTION OF THE INVENTION

Figure 1A:
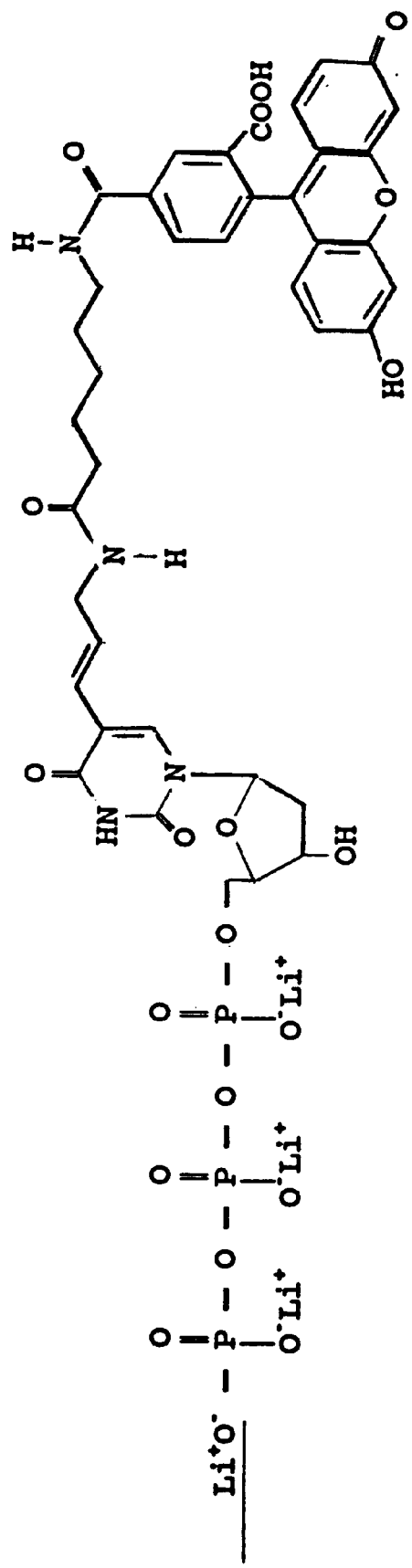

Although naturally-occurring DNA polymerases are in general unsuitable for synthesis of long complementary chains of fluorophore-labeled DNA, mutant DNA polymerases identified by genetic selection have properties which allow for the efficient synthesis of a complementary, fluorophore-labeled DNA. Three types of DNA polymerase modifications are predicted to improve the ability of DNA polymerases to synthesize a complementary fluorophore-labeled DNA: (1) reduction or loss of 3'→5' exonuclease activity present in many naturally-occurring DNA polymerases; (2) increased ability to incorporate fluorophore-labeled nucleotides; and (3) increased ability to extend fluorophore-labeled DNA. Elimination or reduction of 3'→5' exonuclease activity would be expected to prevent removal of incorporated fluorophore-labeled nucleotides, while increased incorporation and extension of fluorophore-labeled nucleotides would allow for efficient synthesis of fluorophore-labeled complementary DNAs. Loss of 3'→5' exonuclease activity, however, would reduce the accuracy of DNA replication. Thus, an ideal DNA polymerase for synthesis of fluorophore DNA would be an enzyme which retains all or some 3'→5' exonucleolytic proofreading activity in order to achieve accurate synthesis, but has increased ability to incorporate fluorophore nucleotides consecutively compared to wild-type DNA polymerase.

The invention is the discovery of variant DNA polymerases that can incorporate modified nucleotides used to synthesize DNA for single molecule sequencing, for DNA probes, and for mass spectrometry sequencing. Reaction conditions with the variant DNA polymerases have also been developed. The essence of the preferred embodiment is that variant T4 DNA polymerases with increased intrinsic processivity have increased ability to synthesize a complementary DNA with a variety of modified nucleotides. The resulting modified DNAs can be used in a variety of applications, but not limited to, DNA sequencing including single molecule and mass spectrometry methods, and DNA probes.

In accordance with one preferred embodiment of the present invention, there is employed a bacteriophage T4 mutant DNA polymerase with increased ability to synthesize complementary fluorophore-labeled DNAs. An exemplary T4 mutant DNA polymerase suitable for use in accordance with the present invention is the L412M-DNA polymerase. In the above nomenclature, which is used herein throughout, the single letter code for amino acids is used. The numbers flanked by the single letter codes for amino acids are the codon numbers. The L412M-DNA polymerase is different from the wild type T4 DNA polymerase by having a methionine residue in place of a leucine residue at position 412. The identification of the L412M-DNA polymerase by genetic selection has been described in U.S. Pat. No. 5,660, 980, and Stocki, S. A., et al., *J. Mol. Biol.*, 254:15–28 (1995), these disclosures are hereby incorporated by reference in their entirety.

Biochemical studies demonstrate that the L412M-DNA polymerase retains 3'→5' exonuclease activity, is more efficient in primer-extension, and has greater intrinsic processivity. Processivity is defined as the number of enzymatic steps carried out per enzyme encounter with the DNA substrate. Intrinsic processivity is defined as the processivity of the DNA polymerase alone without the addition of accessory proteins. The L412M-DNA polymerase also has greater ability to bind modified primer termini as demonstrated for fluorophore-, biotin- and DIG-modified primer termini and for primer termini with the base analog, 2-aminopurine.

The increased intrinsic processivity of the L412M-DNA polymerase is the distinguishing characteristic of this variant DNA polymerase which allows the enzyme to more efficiently incorporate modified nucleotides and to extend primer-termini with primers containing modified nucleotides. It is known that polymerases, such as bacteriophage T7 DNA polymerase, may be used in conjunction with their accessory proteins thereby increasing the processivity of the polymerase by decreasing the rate of disassociation of the polymerase from the DNA strand to be sequenced. In the case of the T4 polymerase, its accessory proteins, include but are not limited to, the following T4 gene products: gene product 32, 41, 45 and the 44/62 complex. Although DNA polymerase accessory proteins enhance DNA polymerase processivity, the DNA polymerase intrinsic processivity determines if the DNA polymerase will be able to form an active DNA:DNA polymerase complex. Thus, enhanced processivity conferred by accessory proteins is secondary to the intrinsic processivity of the DNA polymerase.

Bacteriophage T4 DNA polymerase is a member of a large group of protein sequence related DNA polymerases called Family B DNA polymerases [Braithwaite, D. K., et al., *Nucl. Acids Res.*, 21:787–802 (1993)]. Of particular relevance are the DNA polymerases from phages T2 and T6 which have extensive protein sequence homology to T4 DNA polymerase. The L412M amino acid substitution resides in a highly conserved DNA polymerase motif called Motif A [Delarue, M., et al., *Protein Eng.*, 3:461–467 (1990)]. Thus, amino acid substitutions in the Motif A sequence in other family B DNA polymerases may convert these DNA polymerases into enzymes with enhanced ability to extend primer-termini, with greater intrinsic processivity, and with greater ability to synthesize complementary DNAs with fluorophore-labeled nucleotides or with other modified nucleotides.

Similarly, other modifications to motif A and to other regions identified by genetic selection produce mutant DNA polymerases with properties advantageous for increased incorporation of fluorophore nucleotides which include increased processivity and increased extension of modified primer termini.

The following amino acid substitutions produce mutant DNA polymerases with properties similar to those of the L412M-DNA polymerase. These polymerases were initially identified and isolated by genetic selection described in Stocki, S. A., et al., *J. Mol. Bio.*, 254:15–28 (1995). The DNA polymerases with asterisks (*) are now under active study, and have so far been shown to be like the L412M-DNA polymerase, in having increased ability to synthesize fluorophore-labeled DNA.

(*) Q380K (lysine substituted for glutamine at position 380)

(*) E395K (lysine substituted for glutamate at position 395)

(*) E743K (lysine substituted for glutamate at position 743)

M725I (isoleucine substituted for methionine at position 725)

M725V (valine substituted for methionine at position 725)

S756P (proline substituted for serine at position 756)

L771F (phenylalanine substituted for leucine at position 771)

L771H (histidine substituted for leucine at position 771)

[L771+V] (valine inserted following leucine 771)

[L771+D] (aspartate inserted following leucine 771)

V355A (alanine inserted for valine at position 355)

Other suitable DNA polymerases, besides T4 polymerase and/or the above amino acid substitutions, and native, artificially mutagenized or mutant polymerases may be identified and isolated by the genetic selection method described in Stocki, S. A., et al., id. The selected polymerases may then be further selected based on their increased intrinsic processivity, using the methods described below, such as based on their increased ability to incorporate fluorophore and other bulky nucleotides in synthesizing complementary DNA. The preferred DNA polymerases, e.g., mutant DNA polymerases, are characterized by having increased ability to extend primers and increased intrinsic processivity relative to the native polymerases, while retaining 3'→5' exonuclease activity. The preferred DNA polymerases may be novel native DNA polymerases with increased intrinsic processivity compared to known DNA polymerases. The more preferred polymerases further have the ability to synthesize long DNAs with normal dNTPs without dissociation. Once the sequence of a polymerase is known, it can be synthetically produced, e.g., through cloning and recombinant technology using methods known in the art, such as described in Sambrook, et al., *Molecular Cloning: A Laboratory Manual* (Cold Spring Harbor Laboratory Press, 2d ed., 1989) and Ausubel, F. M., et al., *Current Protocols in Molecular Biology*, Greene Publishing Associates, New York (1993).

While the present invention is not limited to any particular theory, it is proposed that the mechanism for improved incorporation of modified nucleotides is due to amino acid substitutions that increase stabilization of DNA in the polymerase active center. Thus, any amino acid substitutions that increase stabilization of DNA in the polymerase active center have the potential to produce a mutant DNA polymerase with increased ability to incorporate modified nucleotides, e.g., to synthesize fluorophore-labeled DNA. These amino acid substitutions are now identified by genetic selection. In the future, structural information from DNA polymerase-DNA complexes may provide this information. These studies are with bacteriophage T4 DNA polymerase, but other DNA polymerases with amino acid changes that increase stability of DNA in the polymerase active center would also likely have increased ability to incorporate fluorophore and other bulky nucleotides. Due to extensive sequence homology with T4 DNA polymerase, DNA polymerases such as phages T2 (SEQ ID NO: 1 and 2) and T6 DNA polymerases are particularly suitable in the application of the methods of the invention.

Combinations of amino acid changes are also of interest as multiply mutant DNA polymerases may demonstrate a further increase in the ability to incorporate modified, e.g., fluorophore nucleotides. For example, the E395K+L412M-DNA polymerase, the L412M+E743K-DNA polymerase, the E395K+L412M+E743K-DNA polymerase, and the Q380K+L412M+E743K-DNA polymerase are of interest.

Some Family B DNA polymerases are used commercially, e.g. the Vent (commercially available from New England BioLabs, Inc., Beverly, Mass.) and Pfu DNA polymerases. Unlike the T4 DNA polymerases, these enzymes are thermally stable. These enzymes have the conserved leucine residue in the motif A sequence, and substitution of a methionine residue for this conserved leucine or other amino acid substitutions in the Motif A sequence may allow these enzymes to be used in synthesizing modified, e.g., fluorophore-labeled DNA.

Pursuant to the present invention, it has been determined that contrary to expectations 3'→5' exonuclease activity may be an asset in single molecule sequencing methods. The 3'→5' exonuclease activity of DNA polymerases functions to remove misincorporated nucleotides. If 3'→5' exonuclease activity is reduced, incorrect nucleotides at the primer-terminus cannot be removed. Because these mismatched primer-termini are poor substrates for further extension, further elongation of the DNA chain is prevented. A mutant DNA polymerase with increased ability to incorporate fluorophore nucleotides consecutively but retaining 3'→5' exonuclease activity has been found to be a particularly useful enzyme for synthesis of fluorophore-labeled complementary DNA.

For DNA probe synthesis, the L412M-DNA polymerase and an exonuclease deficient form of the L412M-DNA polymerase are useful. Less accuracy is required for the synthesis of the shorter fluorophore-labeled DNA probes. Exonuclease deficiency was found to improve incorporation of some fluorophore and other modified nucleotides. Specifically, the triply mutant D112A+E114A+L412M-DNA polymerase, where the D112A and E114A amino acid substitutions remove most but not all of the 3'→5' exonuclease activity, was found to have improved incorporation of fluorophore, biotin, DIG and other modified nucleotides.

The wild type bacteriophage T4 DNA polymerase gene has been cloned and the protein product expressed [Lin, T.-C., et al., *Proc. Natl. Acad. Sci. U.S.A.*, 84:7000–7004 (1987); U.S. Pat. No. 4,935,361]. Standard oligonucleotide-directed mutagenesis procedures were used to construct the L412M-DNA polymerase mutant gene for expression of large quantities of the mutant L412M-DNA polymerase. Large amounts of the L412M-DNA polymerase have been purified by a previously described method [Reha-Krantz, L. J., et al., *J. Virol.*, 67:60–66]. Using these same procedures, a large amount of exonuclease-deficient form of the L412M mutant, the triply-mutant D112A+E114A+L412M DNA polymerase, has been produced. The Q380K-, E395K- and E743-DNA polymerases were also constructed similarly.

In accordance with one aspect of the invention, there are provided methods for synthesizing long chains of complementary fluorophore-labeled DNA. The methods employ variant (mutant) DNA polymerases, characterized by having increased ability to extend primers and increased intrinsic processivity relative to native T4 polymerase, while retaining 3'→5' exonuclease activity. For example, the mutant enzyme L412M-DNA polymerase differs from the wild type T4 DNA polymerase by having increased ability to extend primers and by having increased intrinsic processivity; however, like the wild type T4 DNA polymerase, the L412M-DNA polymerase retains an active 3'→5' exonuclease activity. Because the L412M-DNA polymerase is a derivative of the highly accurate T4 DNA polymerase and because the 3'→5' exonuclease activity is retained, DNA products synthesized by the L412M-DNA polymerase are accurate. The increased ability to extend primers and enhanced intrinsic processivity are conferred by a methionine amino acid substitution at position 412 in the T4 DNA polymerase in place of the leucine residue. The L412M-DNA polymerase, by virtue of its new properties, also has improved ability to incorporate other modified nucleotides and thus to synthesize other types of modified DNA. For example, the L412M-DNA polymerase has been used to incorporate biotin-dCMP to make biotin-labeled DNA. Other amino acid substitutions, Q380K, E395K, E743K and others noted above confer similar properties.

In accordance with another aspect of the invention, there are provided methods which are directed at implementing the single molecule sequencing method. The synthetic component of this method requires the synthesis of a complementary fluorophore-labeled DNA by a DNA polymerase. Methods to direct synthesis to one strand of the duplex DNA are described. These methods, although useful to the single molecule sequencing method, may also be of use to other applications which require the synthesis of long chains of fluorophore-labeled DNA.

Several mutant T4 DNA polymerases identified by genetic selection were tested for their ability to synthesize complementary fluorophore-labeled DNAs. In addition to the L412M-DNA polymerase (methionine for leucine at position 412), two mutant T4 DNA polymerases with substantially reduced 3'→5' exonuclease activity were also tested: D112A+E114A (alanine substitutions for aspartate at position 112 and glutamate at position 114), and D219A (alanine in place of aspartate at position 219). Biochemical characterizations of the 3'→5' exonuclease deficient enzymes have been previously reported [Reha-Krantz, L. J., et al., *J. Biol. Chem.*, 268:27100–27108 (1993)]. The partially exonuclease deficient G255S-DNA polymerase was also tested [Stocki, S. A., et al., *J. Mol. Biol.*, 254:15–28 (1995)].

In addition, a modified bacteriophage T7 DNA polymerase, Sequenase Version 2.0, was tested. Sequenase has at least two biochemical properties which might be expected to enable this enzyme to efficiently incorporate fluorophore nucleotides. One potentially advantageous property is its high processivity due to the presence of the accessory protein, thioredoxin, as part of the T7 DNA polymerase complex. Another potentially advantageous property is the elimination of 3'→5' exonuclease activity.

Comparisons of the mutant T4 DNA polymerases with Sequenase demonstrated that one of the mutant T4 DNA polymerases, the L412M-DNA polymerase, was superior to Sequenase in synthesizing complementary fluorophore-labeled DNAs. Since the L412M-DNA polymerase retained 3'→5' exonuclease activity while Sequenase and the T4 D112A+E114A and D219-DNA polymerases did not, 3'→5' exonuclease deficiency is not required for synthesis of long chains of complementary fluorophore-labeled DNA. These comparisons also demonstrate that increased ability to extend primers and enhanced intrinsic processivity are useful properties for the synthesis of fluorophore DNAs, because these are properties which distinguish the mutant L412M-DNA polymerase from the wild-type enzyme. Although Sequenase is also processive by virtue of association with thioredoxin, the processivity of the L412M-DNA polymerase differs since the methionine substitution for leucine 412 increases the intrinsic processivity of the DNA polymerase which is independent of accessory processivity proteins. The L412M has high intrinsic processivity which is increased in the presence of association of the DNA polymerase with accessory proteins.

An additional requirement in the synthesis component of the single molecule sequencing method is that complementary fluorophore-labeled products be synthesized with high fidelity. Wild type T4 DNA polymerase is one of the most accurate DNA polymerases with an error frequency of about $10^{-8}$ errors/base pair [Kunkel, T. A., et al., *J. Biol. Chem.*, 259:1539–1545 (1984)]. The L412M-DNA polymerase is about five- to about ten-fold less accurate.

Studies of the accuracy of DNA replication by the L412M-DNA polymerase with fluorophore dNTPs suggest that the L412M-DNA polymerase accurately incorporates fluorophore-labeled nucleotides. The L412M-DNA polymerase retains 3'→5' exonuclease activity which acts to proofread misincorporated nucleotides. Sequenase lacks 3'→5' exonuclease activity and, thus, has lower DNA replication fidelity than the T4 L412M-DNA polymerase. Furthermore, the lack of 3'→5' exonuclease activity in Sequenase may be the reason why Sequenase is less efficient than the T4 L412M-DNA polymerase in synthesizing long chains of fluorophore-labeled DNA.

DNA polymerases in general cannot efficiently extend mismatched primer-termini. The 3'→5' exonuclease activity acts to repair mismatched primer-termini and thus converts a primer-terminus that is only poorly extendable by a DNA polymerase to a correctly base-paired primer-terminus which is more readily extendable. For Sequenase, which does not have an active 3'→5' exonuclease activity, misincorporated nucleotides may result in mismatched primer-termini which cannot be extended; this may result in premature termination of synthesis. The T4 L412M-DNA polymerase, because of its 3'→5' exonuclease activity, can correct mismatched primer-termini, thereby improving the fidelity of DNA replication. This activity also prevents premature termination of replication. Thus, the DNA polymerase 3'→5' exonuclease activity appears to be an asset by allowing more accurate DNA replication and synthesis of longer products.

In accordance with another aspect of the invention, the T4 L412M-DNA polymerase is employed in combination with another DNA polymerase. In one embodiment, Sequenase is employed in combination with L412M-DNA polymerase. Sequenase is processive and this enzyme was second in efficiency in synthesizing fluorophore-labeled DNAs to the T4 L412M-DNA polymerase. A combination of Sequenase and the L412M-DNA polymerase may in some instances realize the best attributes of both enzymes. Another possible combination is L412M-DNA polymerase and an exonuclease-deficient form of the polymerase (for example, the multiple mutant D112A+E114A+L412M-DNA polymerase). Yet another combination employs the L412M-DNA polymerase and a thermostable DNA polymerase (such as Vent or Vent modified to resemble the properties of the L412M-DNA polymerase).

In accordance with another aspect of the invention, the L412M-DNA polymerase is employed in the synthesis of fluorophore-labeled or other labeled DNAs to be used as probes. DNA probes are typically a few hundred to a few thousand nucleotides in length, with one nucleotide partially or fully substituted by a fluorophore-labeled nucleotide. When the DNA probes are added to the assay system, specific interaction between the DNA probe and the target DNA or RNA is observed due to base pairing between the probe and target DNA or RNA. In order to optimize fluorescence intensity of fluorescent-labeled probes, it is often appropriate to adjust the extent of fluorophore substitution. Instead of 100% fluorophore nucleotide in place of a standard dNTP, a mixture of fluorophore-dNTP and unmodified dNTP is used, with the optimum mixture for any given probe being determined by experiment to see what extent of fluorophore-nucleotide substitution gives the highest fluorescence. In addition to fluorophore nucleotides, this approach for making labeled probes has been successfully employed using other labeled nucleotides, such as biotin-labeled dUTP and biotin-labeled dCTP, and DIG-labeled dCTP.

For purposes of preparing probes and for use with some modified nucleotides, an exonuclease deficient version of the L412M-DNA polymerase may have advantages. For example, the D112A+E114A+L412M-DNA polymerase, while not optimal for use in DNA sequencing, may have particular utility in preparing probes using fluorophore-labeled or other modified nucleotides. Probes are shorter and a population of probes is a modal distribution, not likely to include more than a few copies of the same "mistake" in synthesis. Moreover, even a few mistakes would not prevent the probes from basepairing with the target DNA or RNA. However, for single molecule DNA sequencing single molecules are sequenced, so essentially 100% accuracy is required in those uses.

Temperature is an important parameter in the synthesis of fluorophore DNA. Although synthesis of fluorophore DNA is observed at room temperature, a higher temperature of 42° C. increases replication past secondary structures in the template DNA. The inclusion of 16–18% glycerol in the reactions also assists in the incorporation of modified nucleotides.

The invention may be better understood with reference to the accompanying examples, which are intended for purposes of illustration only and should not be construed as in any sense limiting the scope of the invention as defined in the claims appended hereto.

EXAMPLES

Example 1

Synthesis of complementary fluorophore-labeled DNA was tested using the following procedure. The DNA template was a single-stranded circular DNA of approximately 7000 nucleotides. The template was primed with a single, $^{32}$P-labeled complementary oligonucleotide. The test was to measure how far various DNA polymerases could extend the labeled primer when fluorophore-labeled dNTPs were supplied in place of the standard unmodified dNTPs. After the reaction mixtures were incubated, the primer-extension products were separated by electrophoresis on standard DNA sequencing gels. The size of the reaction products was revealed after exposure of the gels to X-ray film.

Figure 1B:
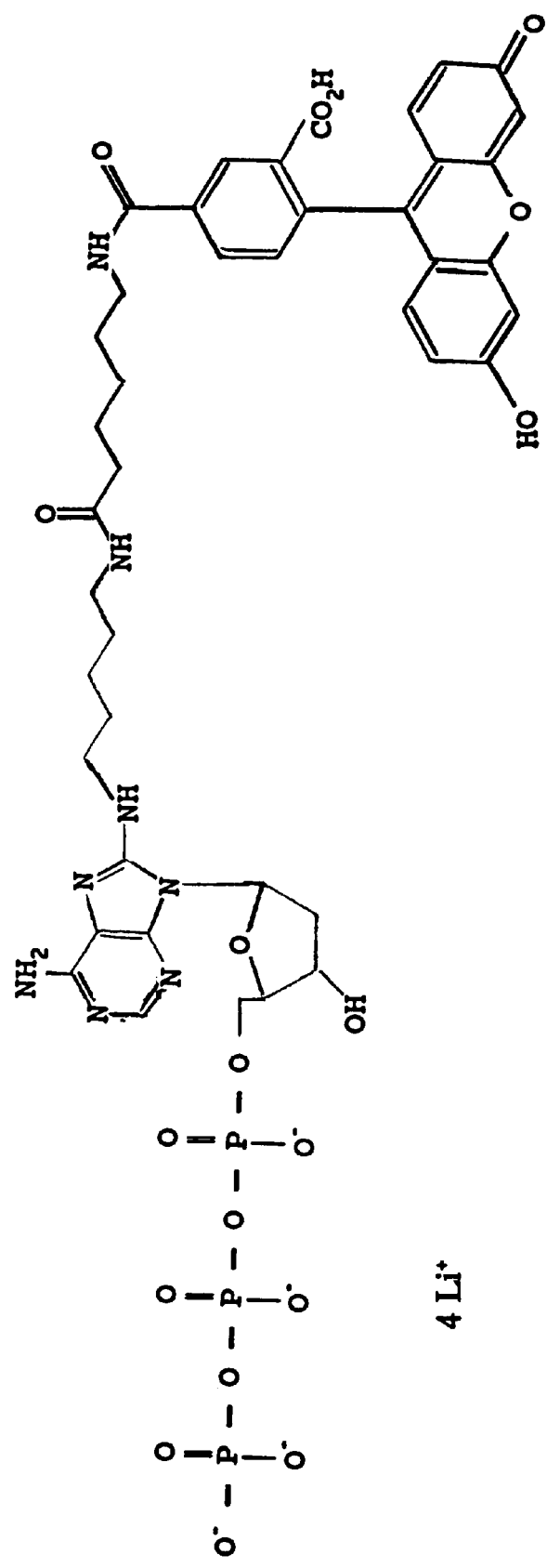
Figure 1C:
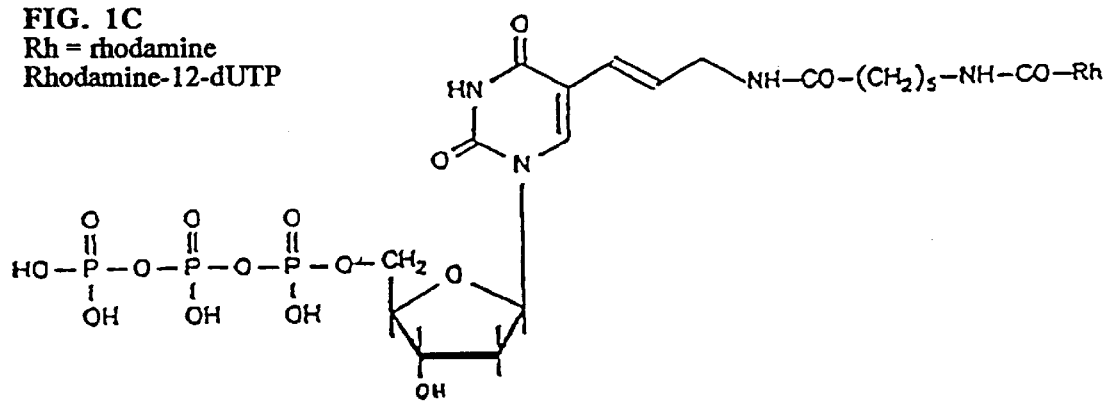
Figure 1D:
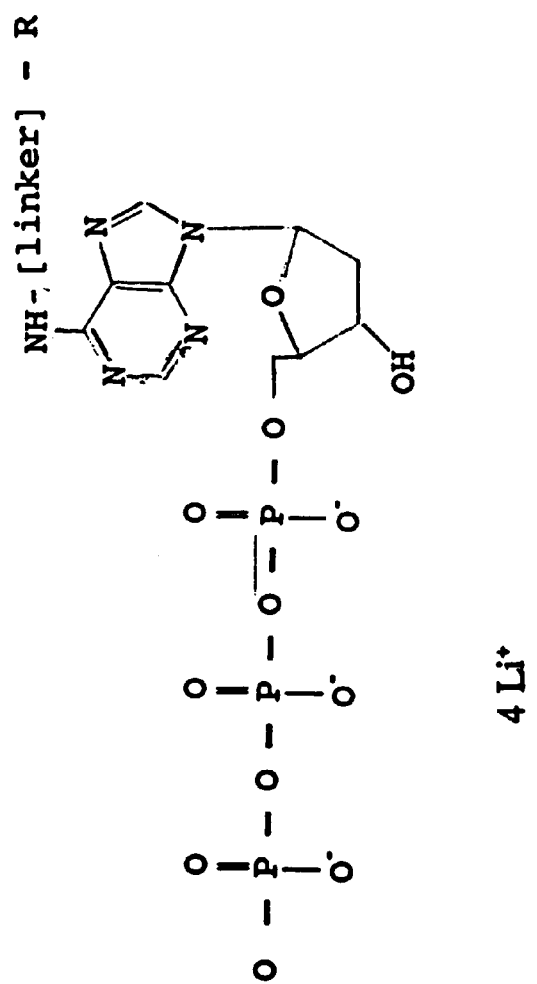

Six fluorophore-labeled nucleotides were tested. Fluorescein-12-2'-deoxy-uridine-5'-triphosphate (FIG. 1A) and fluorescein-15-2'-deoxy-adenine-5'-triphosphate (FIG. 1B) were purchased from Boehringer Mannheim (Indianapolis, Ind.). Rhodamine-12-dUTP (FIG. 1C), rhodamine-dATP (FIG. 1D), rhodamine-dCTP (FIG. 1E), and fluorescein-dCTP (FIG. 1F) were provided by Life Technologies Incorporated, Bethesda, Md.

The reaction mixtures contained 67 mM Tris-HCl (pH 8.8), 16.7 mM $(NH_4)_2SO_4$, 0.5 mM dithiothreitol, 6.7 mM $MgCl_2$, and 167 µg/ml bovine serum albumin. The polymerase concentrations were 0.15–0.3 pmol/ml and the DNA concentration was 7.5 fmol/ml. Nucleotide concentrations, dNTP and fluorophore-labeled dNTPs, were each at 80 µM. The reaction volume was 10 µl. Reactions were incubated at 37° C. for the indicated times.

Fluorescein-12-dUTP (FIG. 1A), rhodamine-12-dUTP (FIG. 1C), rhodamine-dATP (FIG. 1D), rhodamine-dCTP (FIG. 1E) and fluorescein-dCTP (FIG. 1F) were incorporated to variable extents by the DNA polymerases tested. The mutant T4 DNA polymerases and Sequenase performed better than the wild type T4 DNA polymerase. Fluorescein-15-dATP (FIG. 1B) was poorly incorporated by the DNA polymerases tested and was, thus, found less suitable for use in the synthesis of fluorophore-labeled DNA.

Figure 2A:
FIGS. 2A and 2B depict the DNA sequencing gels which demonstrate the superior ability of the L412M-DNA polymerase to synthesize complementary fluorophore-labeled DNAs (2A) and plasmid DNA with Rhodamine-dUTP by wild type and L412M-DNA polymerases (2B)

The single molecule sequencing method requires that two or more fluorophore-nucleotides be substituted for standard, unmodified nucleotides. Reactions with pairwise combinations of the fluorophore nucleotides provide useful information about the efficacy of various DNA polymerases for the synthesis of fluorophore-labeled DNAs. Reactions with the exonuclease deficient T4 D219A-DNA polymerase, the T4 L412M- and G255S-DNA polymerases, and the Klenow fragment of *E. coli* DNA pol I are shown in FIG. 2A. Reactions were incubated for 18.5 hours at 37° C. Reactions in lanes a–d contain rhodamine-dATP (FIG. 1D) in place of dATP. Reactions in lanes e–h contain rhodamine-dCTP (FIG. 1E) in place of dCTP. Reactions in lanes i–l contain the combination of rhodamine-dATP and rhodamine-dCTP in place of dATP and dCTP. Under all conditions, the longest complementary fluorophore-labeled products were synthesized by the T4 L412M-DNA polymerase which has increased intrinsic processivity (FIG. 2A, lanes b, f and j). The G255S-DNA polymerase (FIG. 2, lanes c, g and k) was not as efficient. The exonuclease deficient DNA polymerases, the D219A-DNA polymerase (FIG. 2, lanes a, e and i) and the D112A+E114A-DNA polymerase (data not shown) were also not as efficient as the L412M-DNA polymerase. The Klenow fragment reactions were also less efficient (lanes d, h and l).

Reaction products were shorter when two fluorophore nucleotides were used (FIG. 2A, lanes i–l). It is likely that the size of the products with rhodamine-dATP and dCTP is an underestimate of the ability of the enzymes to synthesize fluorophore-labeled DNA, because the fluorophore is attached to the bases at hydrogen bonding positions; attachment at hydrogen bonding positions affects base pairing. Nucleotides with modifications that do not affect base pairing positions are expected to be more efficiently incorporated.

The next test was to determine if the L412M-DNA polymerase could synthesize a full-length copy of plasmid DNA if rhodamine-12-dUTP (FIG. 1C) was substituted for TTP. The reaction conditions were further optimized and contained 18% glycerol, 67 mM Tris-HCl (pH 8.8), 16.7 mM $(NH_4)_2SO_4$, 0.5 mM dithiothreitol, 6.7 mM $MgCl_2$, and 167 µg/ml BSA. Rhodamine-dUTP and dATP, dCTP, and dGTP were at 200 µM. There was a ten-fold excess of the L412M-DNA polymerase over singly primed, single-stranded plasmid DNA molecules. Reactions were incubated at 42° C. Reaction products were separated on 0.5% agarose gels in ethidium bromide. The primer was labeled with $^{32}$P so that reaction products could be visualized by exposing the gels to X-ray film.

Figure 2B:
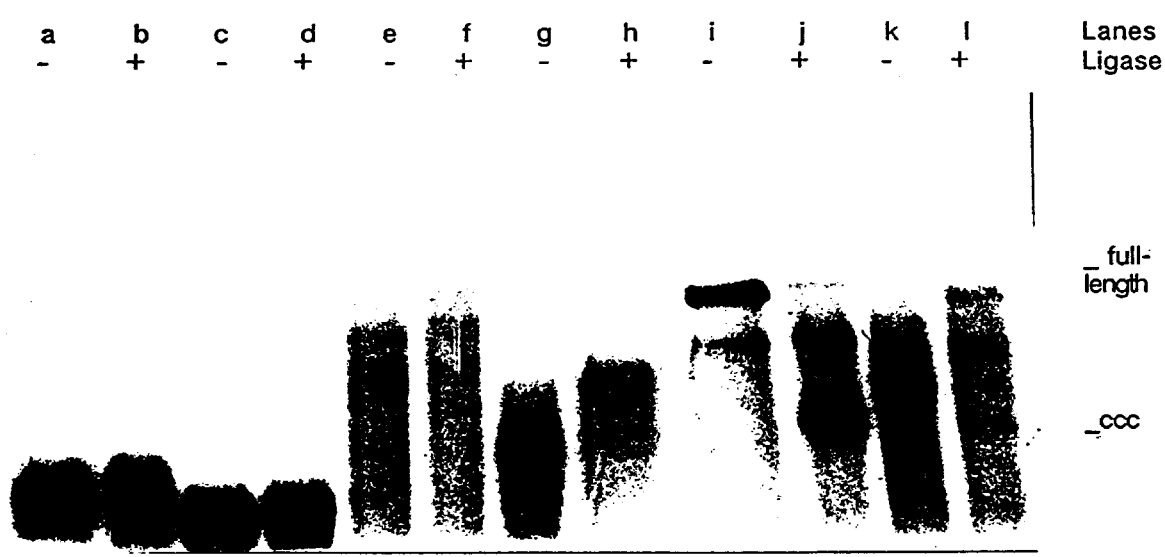

FIG. 2B illustrates the results of synthesis of plasmid DNA with Rhodamine-dUTP by wild type and L412M-DNA polymerases. Wild-type and the L412M-DNA polymerases were incubated for 5 min (lanes a–d), 30 min (lanes e–h), and 60 min (lanes i–l) at 42° C. Lanes a and b, e and f, and i and j contain reaction products with the L412M-DNA polymerase. Lanes c and d, g and h, and k and l contain reaction products with the wild-type T4 DNA polymerase. At 5 min and at 30 min, reaction products for the L412M-DNA polymerase (lanes a, b, e, f) had lower mobilities and are thus longer than products synthesized by the wild type T4 DNA polymerase (lanes c, d, g, h).

T4 DNA ligase and ATP were added to some of the reactions to measure production of full-length plasmid DNA. The presence of ligase is indicated by a "+" above the lanes; no ligase is indicated by a "−". When primed circular plasmid DNAs are fully replicated, the 3'-end of the synthesized DNA can be ligated to the 5'-end of the primer. Thus, full-length DNA can be seen as DNA which can be converted to covalently closed circular DNA (ccc DNA) by the action of ligase. Covalently closed circular plasmid DNA has a faster mobility than plasmid DNA with gaps or nicks. The mobilities of fully replicated plasmid DNA that has not been ligated and fully replicated ligated DNA are indicated in FIG. 2B. Significantly higher amounts of full-length plasmid DNA (lane i) and covalently closed circular DNA (lane j) are produced by the L412M-DNA polymerase compared to wild-type T4 DNA polymerase (lanes k and l). Longer incubations or increased concentrations of enzyme did not improve the ability of the wild-type T4 DNA polymerase to synthesize full-length plasmid DNA (results not shown). Thus, the L412M-DNA polymerase has superior ability to replicate DNA using rhodamine-dUTP in place of TTP.

Additional bands are apparent, especially in lanes i–l of FIG. 2B. These bands represent sites on the DNA template which are difficult to replicate such as the M13 origin of replication. The L412M-DNA polymerase can more readily replicate past these difficult sites. Similar results have been obtained for the Q380K, E395K, and E743K T4 DNA polymerases.

Figure 3A:
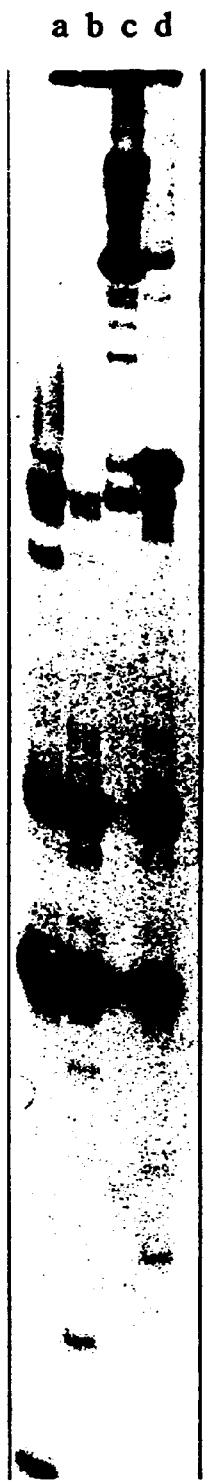
FIG. 3A depicts the DNA sequencing gels which demonstrate that the L412M-DNA polymerase is superior to Sequenase in the synthesis of complementary fluorophore-labeled DNAs.

Reactions with rhodamine-dUTP and rhodamine-dCTP were done for the L412M-DNA polymerase and compared to Sequenase (FIG. 3A). Reactions in lanes a and c contain the T4 L412M-DNA polymerase. Reactions with Sequenase are in lanes b and d. Reactions in lanes a and b were incubated for 30 min at 37° C., reactions in lanes c and d were incubated for 18.5 hours. The L412M-DNA polymerase produced the longest products (lanes b and d).

Example 2

Figure 3B:
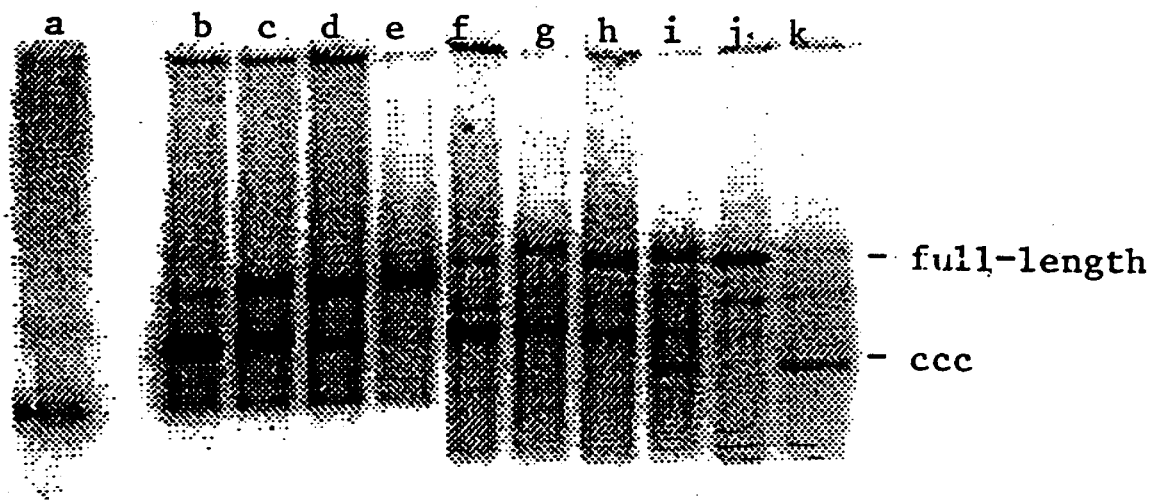
FIG. 3B depicts the gels which demonstrate the importance of glycerol in the reaction mixture.

This example demonstrates the importance of glycerol in the reaction mixture (FIG. 3B). The L412M-DNA polymerase (1 pmol) was incubated in reaction mixtures with 67 mM Tris-HCl (pH 8.8), 16.7 mM $(NH_4)_2SO_4$, 0.5 mM dithiothreitol, 6.7 mM $MgCl_2$, 167 µg/ml bovine serum albumin (BSA), 200 µM dCTP, dGTP, and dATP and rhodamine dUTP, and 0.1 pmol primed, single-stranded plasmid DNA. All reactions were incubated at 42° C. for 90 min. The reaction products were separated on a 0.5% agarose gel. Lane a is the control and shows the mobility of the primed single-stranded DNA. The reaction mixtures in lanes b and c contained 6.5% glycerol in addition to the above listed reaction components. Lanes d and e contained 7.5% glycerol. Lanes f and g contained 11.25% glycerol. Lanes h and i contained 13.75% glycerol Lanes j and k contained 16.25% glycerol. Lanes c, e, g, i and k also contained DNA ligase and ATP. As the glycerol concentration was increased, longer fluorophore-labeled DNAs were produced as demonstrated by the increases in full-length (lanes f–j) and cccDNA (lanes i and k).

Example 3

In order to use the L412M-DNA polymerase for the synthesis of complementary fluorophore-labeled DNAs, alone or in combination with accessory proteins and/or the gene 32 protein, the enzyme is directed to one of the two potential sites for DNA polymerase action that exist on each linear duplex DNA. The following procedure is designed so that users will be able to convert long pieces of duplex DNA, tens of thousands of nucleotides in length, to duplex DNA in which one of the complementary strands contains fluorophore-labeled DNA and in which each duplex DNA contains the means to anchor the duplex DNA to a streptavidin-coated bead. The bead-fluorophore DNA complex is immobilized in a flow cell for the digestion and the detection of fluorophore dNMPs which are the next steps of the single molecule sequencing method. The means already exist to immobilize single DNA molecules in a flow cell [Ambrose, et al., *Ber. Busenges Phys. Chem.*, 97:1535 (1993)]. The following procedure provides a method to synthesize long chains of complementary DNA in a form which can be immobilized in a flow cell in preparation for the digestion and detection steps of the single molecule sequencing method and other DNA sequencing methods which rely on fluorophore-labeled DNA. This method could also be adapted for use in preparing other types of modified DNA, for DNA amplification and for cloning procedures.

First, genomic and/or chromosomal DNA is prepared to minimize breaking of the DNA. Known methods for preparation of high molecular weight DNA, such as immobilization in agarose, may be employed [Ausebel, et al, *Current Procedures in Molecular Biology.*, 1:2.5.11 (1995)]. The next step is to digest the high molecular weight DNA, which may be intact chromosomes, with a restriction endonuclease which cuts DNA only infrequently so that the cut DNA fragments are still for the most part several thousand or tens of thousands of nucleotides in length. The next step is to convert these long duplex DNAs into substrates so that one of the duplex strands can be converted into the complementary fluorophore-labeled strand. A procedure to achieve synthesis of a complementary fluorophore-labeled DNA is depicted in FIG. 4.

The linear duplex DNAs that result from restriction endonuclease cleavages have two complementary ends. In the drawing in FIG. 4A, two 5' overhanging four nucleotide complementary ends are indicated for the model linear duplex DNA Linear duplex DNAs also have two 3' ends that can be used by DNA polymerases. In order to limit DNA polymerase activity to a single 3' end, one end is blocked by annealing a self-complementary hairpin DNA which has an unpaired end that is complementary to the restriction endonuclease cut linear duplex DNA.

Figure 4:
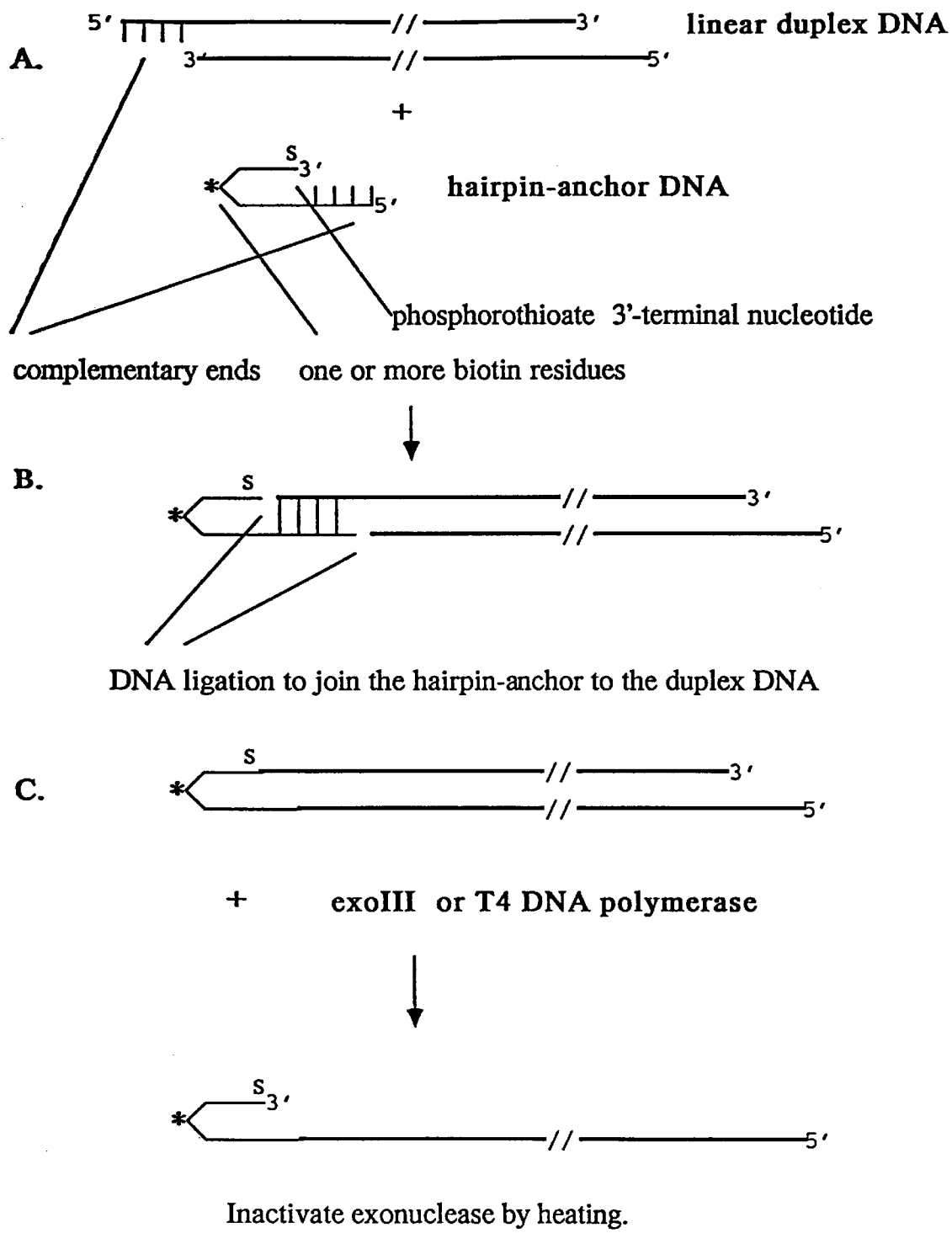
FIG. 4 depicts the steps of an exemplary procedure for synthesis of complementary fluorophore-labeled DNAs for single-molecule DNA sequencing.
Figure 4:
Figure 4:
Figure 4:
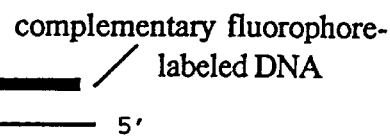
Figure 4:
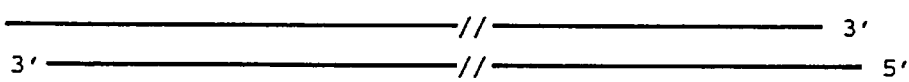
Figure 4:
Figure 4:
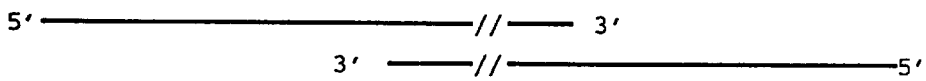
Figure 4:
Figure 4:
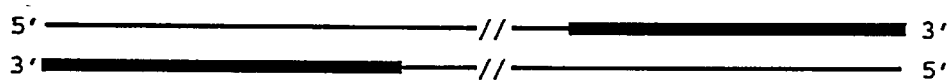
Figure 4:
Figure 4:
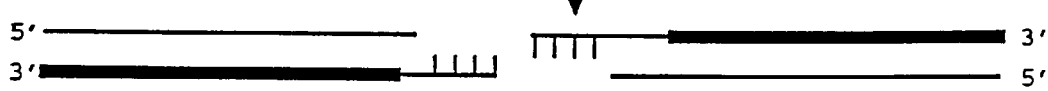

The hairpin-anchor DNA is covalently joined to the linear duplex DNA by DNA ligation (FIG. 4B). One important feature of the hairpin DNA is that this DNA contains one or more biotin residues which are used to anchor the DNA to a streptavidin-coated bead which is required in a later step in the single molecule sequencing method (biotin is indicated by a "*" in FIG. 4).

A further important feature of the hairpin-anchor DNA is that there is a phosphorothioate group in the linkage joining the 3'-terminal nucleotide (the phosphorothioate containing linkage is indicated by an "s" in FIG. 4). When the phosphorothioate linkage is formed, two diasteriomers are made in about equal amounts. One of the phosphorothioate interlinkages is hydrolyzable by the 3'→5' exonuclease activity of T4 DNA polymerase, while the second is resistant [Romaniuk, P., et al., *J. Biol. Chzem.*, 257:7684–7688 (1982); Gupta, et al., *J. Biol. Chem.*, 257:7689–7692 (1982)]. The nonhydrolyzable internucleotide linkage protects DNA 5' to the linkage from digestion.

After the hairpin-anchor DNA is joined by DNA ligation to the linear duplex DNA, the resulting joint DNA molecule has a single 3'-end and a single 5'-end (FIG. 4B). The 5'-end has an unpaired DNA sequence complementary to restriction endonuclease cut DNA. Restriction endonucleases are known which cut DNA infrequently so that chromosomal DNA is fragmented into linear duplex DNAs several thousand or tens of thousands nucleotides in length. Hairpin-anchors can be prepared with complementary ends to match these selected nucleases. The hairpin-anchor DNA also has self-complementary sequences with an intervening loop sequence. The self-complementary sequences can vary, but the base pairing between the sequences must be of sufficient stability so that the hairpin structure forms readily under experimental conditions. The loop sequence can also vary, but the loop sequence must not destabilize the hairpin structure and it must contain one or more biotin residues.

The 3'-end of the hairpin-anchor DNA has the phosphorothioate linkage. Existing automated DNA synthesis procedures using phosphoramidite chemistry can be used for the synthesis of the hairpin-anchor DNA. The two phosphorothioate isomers of the hairpin-anchor DNA are produced in about equal amounts from the synthesis. The isomer which is nonhydrolyzabie by T4 DNA polymerase can be prepared by treating the mixture of hairpin-anchor DNAs with T4 DNA polymerase under DNA digestion conditions. Only the nonhydrolyzable hairpin-anchor DNA remains after the digestion reaction is completed.

A variation of the steps depicted in FIGS. 4A and B is to join the hairpin-anchor DNA to the linear duplex DNA by blunt-end ligation. Linear duplex DNA can be prepared by restriction endonuclease digestion as above or by other methods that fragment the DNA into large pieces, such as shearing the DNA. The fragmented DNA is then made blunt-ended using standard procedures [Ausebel, et al., *Current Procedures in Molecular Biology*, (1995)]. For this application, a blunt-ended hairpin-anchor is prepared, but this DNA still retains the biotin and phosphorothioate modifications as indicated in FIG. 4A. Blunt-end ligation conditions are then used to join the hairpin-anchor DNA to the linear duplex DNA so that usually only a single hairpin-anchor DNA is joined to each linear duplex DNA. One advantage to this method is that a single universal hairpin-anchor DNA would be sufficient. Another advantage is that it may be useful for some DNA sequencing projects to have methods other than restriction endonuclease cleavage for fragmenting DNA.

The joint hairpin-anchor:linear duplex DNA is then treated with the T4-DNA polymerase under conditions so that the 3'→5' exonuclease activity is functioning, but not the polymerase activity. Selective activation of the 3'→5' exonuclease is achieved simply by not including dNTPs in the reaction mixture. One suitable reaction buffer contains 18% glycerol, 50 to 70 mM Tris-HCl (pH 7.0 to 8.8), 5 to 7 mM MgCl$_2$, 16.7 mM (NH$_4$)$_2$SO$_4$, 0.5 mM dithiothreitol, and 0.2 mg/ml bovine serum albumin. Reaction mixtures are incubated between 37° C. to 42° C.

After exonuclease digestion the joint hairpin-anchor:duplex DNA is degraded partially or until the enzyme reaches a nonhydrolyzable phosphorothioate linkage. The advantage of preparing a hairpin-anchor DNA with a phosphorothioate linkage is now apparent. If the nonhydrolyzable linkage were not present, DNAs may be degraded so far that the primer is lost. A primer is required by DNA polymerases for the synthesis of a complementary DNA.

In order to convert the T4-DNA polymerase from a 3'→5' exonuclease to a polymerase, dNTPs are added. If fluorophore-labeled dNTPs are added, the DNA product synthesized by the polymerase is fluorophore labeled. The synthesis of the complementary fluorophore-labeled DNA product by the L412M-DNA polymerase may be enhanced by the addition of T4 DNA polymerase accessory proteins such as the products of T4 genes 44, 45 and 62 and/or the T4 single-stranded DNA binding protein, the product of gene 32. Alternatively, a mixture of DNA polymerases, such as the T4 L412M-DNA polymerase plus Sequenase, may be employed.

Another variation is to use a hairpin-anchor DNA that lacks the biotin residue. Biotin-labeled dUTP is incorporated readily by the T4 DNA polymerase [Langer, P. R., et al., *Proc. Natl. Acad. Sci. U.S.A.*, 78:6633–6637 (1981)]. If biotin-labeled dUTP is incubated for a short time with dATP, dCTP, and dGTP and the L412M-DNA polymerase, the joint hairpin-anchor:duplex DNA is labeled with one or more biotin residues. Joint hairpin-anchor:duplex DNAs with two hairpin-anchor DNAs will not be labeled with biotin; DNAs with no hairpin-anchor DNA will have been digested (FIG. 4C). Streptavidin-coated beads can then be added to extract the biotin-labeled hairpin-anchor:duplex DNAs and to trap unincorporated biotin-labeled dUTP. The unincorporated dNTPs can be washed away. The fluorophore dNTPs can then be added along with the L412M-DNA polymerase and accessory proteins as needed to complete the synthesis of the complementary fluorophore labeled DNA. One potential advantage of using this procedure is that joint hairpin-anchor:duplex molecules with a single hairpin-anchor are selected from the pool of molecules.

An alternative to the steps depicted in FIGS. 4A–4D is to treat linear duplex DNA, with or without a prior fragmentation treatment, with the L412M-DNA polymerase to digest the DNA from both 3'-ends (FIG. 4E). Fluorophore dNTPs are then added along with accessory proteins as needed. The fluorophore modified duplex DNA is resistant to digestion by most restriction endonucleases, but the unmodified duplex DNA will remain sensitive. Addition of a restriction endonuclease that cuts frequently will likely result in fragmenting the DNA in the unmodified region. The restriction cut ends can then be annealed to a hairpin-anchor DNA with a complementary end. DNA ligation links the hairpin-anchor DNA to the fluorophore-labeled DNA. The resulting DNA molecule resembles the final product depicted in FIG. 4D.

Example 4

Synthesis of DNA probes is similar to synthesis of long fluorophore-labeled DNAs for single-molecule sequencing. The primary difference is that DNA probes are shorter. A second difference is that while a high level of substitution of fluorophore nucleotides for non-modified nucleotides is required for single molecule DNA sequencing, less substitution is required to produce DNA probes with the greatest sensitivity. For example, DNA probes containing a high level of fluorescein-dUMP may be less bright than DNA probes with fewer fluorescein-dUMP molecules because of quenching.

Figure 5:
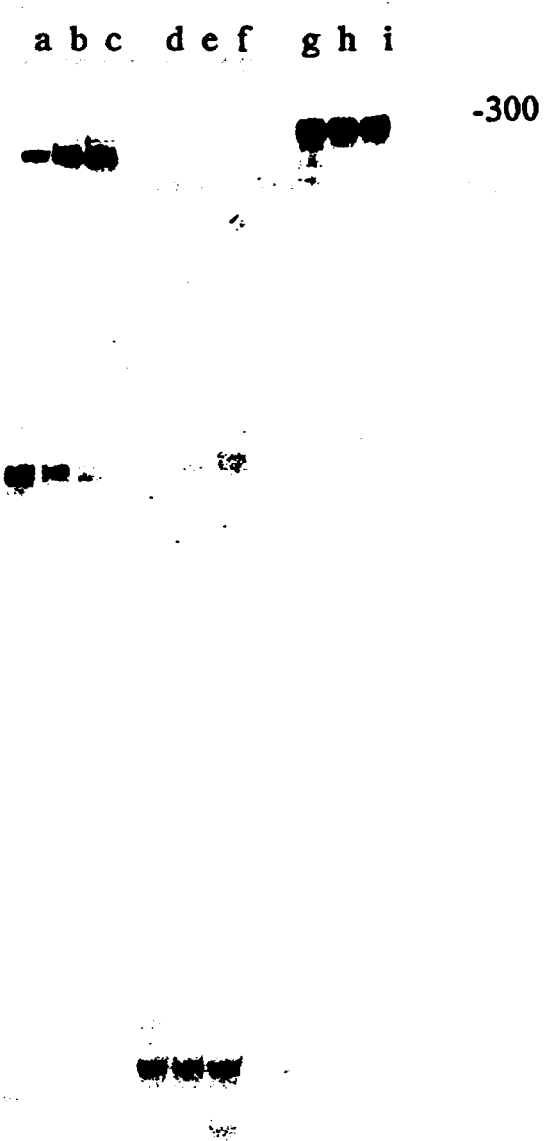
FIG. 5 depicts a DNA sequencing gel which illustrates the synthesis of biotin-, DIG- and fluorophore-labeled probes.

A DNA probe made with rhodamine-dCTP is shown in FIG. 5 (lanes g–i). The reaction conditions were as described for FIG. 2B except that a second oligonucleotide was annealed 300 nucleotides downstream from the primer. The downstream oligonucleotide acts as a block to synthesis and, thus, limits the fluorophore-labeled product to a length of approximately 300 nucleotides.

The reaction conditions are identical to the conditions for FIG. 2B except that reactions contained 200 μM dATP, dGTP and dTTP with 200 μM biotin dCTP (lanes a–c), or 200 μM DIG-dCTP (lanes d–f), or 200 μM rhodamine-dCTP. The reactions were incubated for 5 min (lanes a, d, g), 15 min (lanes b, e, h), and 30 min (lanes c, f, i). The reactions in FIG. 5 contained the L412M-DNA polymerase, but similar results were obtained with the D112A+E114A+L412M-DNA polymerase. A high yield of the 300-nucleotide biotin- (lanes a–c) and rhodamine- (lanes g–i) labeled probes were obtained. Full-length DIG-labeled probe (lanes d–f) was not obtained under these conditions, but longer reaction times increase the yield of full-length probe.

The amount of labeled nucleotide in the product can be varied by using various ratios of modified and non-modified dNTPs in the reactions. One hundred percent (100%) rhodamine-dCTP was used for the reactions in FIG. 5. Fluorescence intensity can be determined by using a fluorimeter. The fluorescence intensity obtained with 100% rhodamine-dCMP substitution can then be compared with DNAs made with less rhodamine-dCMP to determine the optional degree of substitution.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

We claim:

1. A method for synthesizing a complementary DNA, from a DNA template, the improvement comprising: using a mutant Family B DNA polymerase, with increased intrinsic processivity relative to native DNA polymerase, to synthesize a complementary DNA having one or more fluorophore-labeled nucleotides incorporated therein.

2. The method of claim 1, wherein the mutant Family B polymerase is a mutant T4 DNA polymerase selected from the group consisting of L412M-DNA polymerase, Q380K-DNA polymerase, E395K-DNA polymerase, E743K-DNA polymerase, M725I-DNA polymerase, M725V-DNA polymerase, S756P-DNA polymerase, L771F-DNA polymerase, L771H-DNA polymerase, -DNA polymerase, -DNA polymerase, V355A-DNA polymerase, E395K+L412M-DNA polymerase, L412M+E473K-DNA polymerase, E395K+L412M+E743K-DNA polymerase, and Q380K+L412M+E743K-DNA polymerase.

3. The method of claim 1, wherein the mutant Family B polymerase is a multiple mutant T4 DNA polymerase with one or more amino acid substitutions selected from the group consisting of: Q380K, E395K, E743K, M725I, M725V, S756P, L771F, L771H, and V355A.

4. The method of claim 1, further comprising the step of employing the resulting complementary DNA in single molecule sequencing, making DNA probes, or mass spectrometry sequencing.

5. The method of claim 1, wherein the mutant DNA polymerase incorporates at least two different fluorophore-labeled nucleotides into complementary DNA.

6. The method of claim 1 wherein one or more unmodified nucleotides are replaced by the corresponding fluorophore-labeled nucleotides.

7. The method of claim 1, wherein the one or more fluorophore-labeled nucleotides are selected from the group consisting of fluorescein- and rhodamine-labeled nucleotides.

8. The method of claim 1 wherein the mutant Family B DNA polymerase is selected from the group consisting of T2, T4, and T6 mutant DNA polymerases.

9. The method of claim 1 wherein the mutant Family B DNA polymerase has an amino acid substitution in highly conserved Motif A.

10. The method of claim 1, wherein the polymerase is a mixture comprising a first polymerase and a second polymerase, wherein:

a. the first polymerase is a mutant T2, T4, or T6 DNA polymerase selected from the group consisting of L412M-DNA polymerase, Q380K-DNA polymerase, E395K-DNA polymerase, E743K-DNA polymerase, M725I-DNA polymerase, M725V-DNA polymerase, S756P-DNA polymerase, L771F DNA polymerase, L771H-DNA polymerase, -DNA polymerase, -DNA polymerase, V355A-DNA polymerase, E395K+L412M-DNA polymerase, L412M+E473K-DNA polymerase, E395K+L412M+E743K-DNA polymerase, and Q380K+L412M+E743K-DNA polymerase; and b. the second polymerase is selected from the group consisting of an exonuclease deficient DNA polymerase, and a thermostable DNA polymerase.

11. The method of claim 1, wherein the DNA template is primed with a first oligonucleotide.

12. The method of claim 11, wherein further synthesis of the complementary DNA is blocked by a second oligonucleotide.

13. The method of claim 1, wherein the complementary DNA is a full-length copy of the template DNA.

14. The method of claim 1 wherein the DNA template is covalently joined to a self-annealing hairpin DNA.

15. The method of claim 14, wherein the hairpin DNA contains at least one nonhydrolyzable internucleotide linkage.

16. The method of claim 15, wherein the internucleotide linkage is a phosphorothioate linkage.

17. The method of claim 14, wherein the hairpin DNA further comprises means for immobilizing a DNA molecule in a flow cell.

18. The method of claim 17, wherein the hairpin DNA contains one or more biotin residues.

19. The method of claim 1, wherein synthesizing the complementary DNA gives a duplex DNA in which one strand of the duplex DNA contains fluorophore-labeled DNA.

20. The method of claim 19, wherein the DNA template is covalently joined to a self-annealing hairpin DNA.

21. The method of claim 20, wherein the hairpin DNA further comprises means to anchor duplex DNA to a streptavidin-coated bead.

22. The method of claim 1, further comprising immobilizing the complementary DNA in a flow cell and subjecting the complementary DNA to exonuclease digestion.

23. The method of claim 22, further comprising detecting the fluorophore-labeled nucleotides released by the exonuclease digestion.

* * * * *